US010251997B2

(12) United States Patent
Nessel et al.

(10) Patent No.: US 10,251,997 B2
(45) Date of Patent: Apr. 9, 2019

(54) INJECTION DEVICE FOR DELIVERY OF A LIQUID MEDICAMENT WITH MEDICAMENT CONTAINER DISPLACEMENT

(71) Applicant: Sanofi-Aventis Deutschland GMBH, Frankfurt am Main (DE)

(72) Inventors: Christian Nessel, Frankfurt am Main (DE); Daniel Auernhammer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 166 days.

(21) Appl. No.: 15/026,708

(22) PCT Filed: Oct. 16, 2014

(86) PCT No.: PCT/EP2014/072174
§ 371 (c)(1),
(2) Date: Apr. 1, 2016

(87) PCT Pub. No.: WO2015/055747
PCT Pub. Date: Apr. 23, 2015

(65) Prior Publication Data
US 2016/0250411 A1 Sep. 1, 2016

(30) Foreign Application Priority Data
Oct. 18, 2013 (EP) .................................. 13189313

(51) Int. Cl.
*A61M 37/00* (2006.01)
*A61M 5/155* (2006.01)
(Continued)

(52) U.S. Cl.
CPC ........ *A61M 5/155* (2013.01); *A61M 5/14248* (2013.01); *A61M 5/14526* (2013.01);
(Continued)

(58) Field of Classification Search
CPC .... A61M 2005/14252; A61M 5/14248; A61M 5/14526; A61M 5/155; A61M 5/31501
See application file for complete search history.

(56) References Cited

U.S. PATENT DOCUMENTS

| 5,616,132 A | 4/1997 | Newman |
| 2011/0238037 A1* | 9/2011 | Hwang ............. A61M 5/14248 604/506 |
| 2012/0071829 A1 | 4/2012 | Edwards |

FOREIGN PATENT DOCUMENTS

WO WO2011/116304 9/2011

OTHER PUBLICATIONS

International Search Report and Written Opinion in International Application No. PCT/EP2014/072174, dated Jan. 29, 2015, 9 pages.
(Continued)

*Primary Examiner* — Rebecca E Eisenberg
(74) *Attorney, Agent, or Firm* — Fish & Richardson P.C.

(57) ABSTRACT

The present invention relates to an injection device for dispensing of a liquid medicament, the device comprising: a base (10), a medicament reservoir (20) displaceably arranged on the base (10) and containing the liquid medicament (25), an injection needle (30) displaceably arranged relative to the base (10) between a retracted position (30a) and an extended position (30b), a pressure container (40) containing a pressurized fluid (24), a reservoir displacing arrangement (50) coupled with the pressure container (40) to displace the medicament reservoir (20) into a dispensing position (20b), in which the medicament reservoir (20) is in fluid communication with the injection needle (30), a needle displacing arrangement (60) coupled with the pressure container (40) to at least displace the injection needle (30) into the extended position (30b).

16 Claims, 13 Drawing Sheets

(51) Int. Cl.
*A61M 5/145* (2006.01)
*A61M 5/142* (2006.01)
*A61M 5/315* (2006.01)

(52) U.S. Cl.
CPC .................. *A61M 5/31501* (2013.01); *A61M 2005/14252* (2013.01)

(56) References Cited

OTHER PUBLICATIONS

International Preliminary Report on Patentability in International Application No. PCT/EP2014/072174, dated Apr. 19, 2016, 7 pages.
Rote Liste, "50. Hypophyses-, Hypothalamushormone, andere regulatorische Peptide u. ihre Hemmstoffe," Chapter 50, ed. 2008, 20 pages.

* cited by examiner

INJECTION DEVICE FOR DELIVERY OF A LIQUID MEDICAMENT WITH MEDICAMENT CONTAINER DISPLACEMENT

CROSS-REFERENCE TO RELATED APPLICATIONS

This application is a U.S. national stage application under 35 USC § 371 of International Application No. PCT/EP2014/072174, filed on Oct. 16, 2014, which claims priority to European Patent Application No. 13189313.3, filed on Oct. 18, 2013, the entire contents of which are incorporated herein by reference.

FIELD OF THE INVENTION

The present invention relates to the field of injection devices and in particular to automatic injection devices for delivery of a liquid medicament by way of injection.

BACKGROUND

Automatic medicament delivery devices, such like auto-injectors provide a rather easy and convenient approach to inject a predefined dose of a liquid medicament into biological tissue. Such drug delivery devices may provide an injection needle extension and retraction mechanism in order to puncture biological tissue to which the liquid medicament is to be delivered. After the injection needle has been extended into an injection position drug delivery through the injection needle may automatically start. After termination of a delivery process the needle is typically retracted back into the housing. Since such drug delivery devices are intended for home- or self-medication their general handling should be easily understandable and unambiguous.

Additionally, such devices should provide a high degree of patient safety in order to avoid stitch damages or similar injuries. Moreover, depending on the therapy, depending on the medication schedule as well as depending on the size of the dose of the liquid medicament to be injected, in some cases rather large injection volumes, e.g. larger than 1.25 ml and high viscosity of the liquid medicament may cause some difficulties and problems with existing drug delivery device designs. For instance, total time for the delivery of the medicament may be out of a predefined range. Moreover, the viscosity and the total volume of the liquid medicament could lead to patient discomfort.

Since such drug delivery devices are of portable or mobile type they are typically equipped with some kind of energy storage to displace the injection needle and to conduct a dispensing procedure. Document US 2012/0071829 A1 describes an apparatus featuring a medicament injector moveably disposed within a housing and an energy storage member configured to produce a force to move the medicament injector to an injection position in which a portion of a needle is disposed outside of a distal end portion of the housing. The energy storage member is a compressed gas cylinder that is operable to produce a force that acts upon the medicament container to move the same between a first position and a second position. In response to a force produced by the pressurized gas, a moveable member and the medicament injector are moved towards a distal end portion of the housing, thereby exposing the needle from the housing. Then, the moveable member continues to move within the medicament container to expel a medicament from the medicament container through the needle.

For activation of medicament delivery the compressed gas cylinder is to be displaced inside the housing from a first position into a second position, e.g. by way of a suitable spring element. There, not only a well-defined displacement of the compressed gas cylinder but also a gas tight coupling of the gas cylinder has to be provided when it reaches its second position. The housing in which the pressurized gas cylinder is displaced therefore needs to be rather robust and requires a rather precise geometry.

Aspects of the invention may include an improved injection device for dispensing of a liquid medicament featuring an automatic sequence for the various steps of injection and drug delivery. The device should provide a particular high dispensing force, which is even suitable for dispensing and injecting of liquid medicaments featuring a particular high viscosity. Moreover, the injection device should be capable to dispense rather large volumes of liquid medicaments. The device should be user friendly and should provide a tactile and/or an audible feedback to indicate that the injection procedure has terminated. Additionally, the injection device should provide automatic injection needle extension and retraction prior to and after drug delivery. Additionally, the injection device should be rather lightweight. It should be easy to assemble and should be producible in a cost-efficient way, in particular by way of an industrial mass production process

SUMMARY OF THE INVENTION

In a first aspect, an injection device for dispensing of a liquid medicament is provided. The device comprises a base, typically serving as a platform to mount or to assemble various components of the injection device. The base may form part of a housing or may be encapsulated in or by a separate housing of the injection device.

The injection device further comprises a medicament reservoir displaceably arranged on the base and containing the liquid medicament. Typically, the medicament reservoir is displaceable relative to the base at least between an initial position and a dispensing position. By way of displacing the medicament reservoir on and/or relative to the base, a medicament reservoir initially sealed and sterilized can be deployed for medicament delivery just before the medicament delivery will take place. In this way, the shelf life of the injection device can be extended. Additionally, the injection device comprises an injection needle displaceably arranged relative to the base between a retracted position and an extended position. The injection needle may be directly or indirectly mounted on the base. In its retracted position, the injection needle is located on or at an inside-facing portion of the base.

In other words, in the retracted position the injection needle; at least its punctured injection end is located inside a housing. When displaced in the extended position at least a tipped dispensing end of the injection needle protrudes from the base or protrudes from a housing of the injection device. Typically, the base or a respective housing of the injection device is attached to the skin of a patient. By displacing the injection needle from the retracted position to the extended position, the dispensing end of the injection needle punctures and penetrates the patient's skin for the purpose of medicament delivery or medicament injection.

The injection device further comprises a pressure container containing a pressurized fluid. The pressure container may comprise a pressurized gas or a gas liquid mixture. The pressure container typically serves as an energy source to provide mechanical energy at least for displacing the injection needle, for displacing the medicament reservoir and for conducting the process of medicament delivery.

Additionally, the injection device comprises a reservoir displacing arrangement coupled with the pressure container to displace the medicament reservoir into a dispensing position. In the dispensing position the medicament reservoir is in fluid communication with the injection needle. Typically, the fluid communication between the medicament reservoir and the injection needle is just established by the displacing of the medicament reservoir into the dispensing position. In this way, an initially sealed medicament reservoir, such like a standard cartridge or carpule can be used, which may be advantageous in terms of assembly and filling of the cartridge. In other embodiment, the medicament reservoir may be flexible and may for instance comprise a flexible bag.

The injection device also comprises a needle displacing arrangement coupled with the pressure container to at least displace the injection needle into the extended position. By means of the needle displacing arrangement the injection needle is displaceable into the extended position only under the action of a pressurized fluid provided by the pressure container. In a similar way also the medicament reservoir can be displaced only under the action of the pressurized fluid emanating from the pressure container. Since the needle displacing arrangement as well as the reservoir displacing arrangement are both coupled with the pressure container the pressurized fluid may directly act on the needle displacing arrangement as well as on the reservoir displacing arrangement.

By way of a direct coupling of the reservoir displacing arrangement with the pressure container and by way of a direct coupling of the needle displacing arrangement with the pressure container reservoir and needle displacement can take place in a well-defined and precise way. The direct coupling of the pressure container with both, the reservoir displacing arrangement and the needle displacing arrangement provides the benefit, that the sequence of reservoir displacing and needle displacing can be easily adapted and modified according to given requirements of a particular therapy.

Moreover, the pressure container may be fixed relative to the base and/or on the base. In this way, the number of moveable components of the injection device can be reduced, thereby improving operational safety and operability of the injection device. Moreover, by making use of a fixed pressure container constructional demands in regard of mechanical stability and rigidity of the base or of a housing of the injection device can be reduced. This allows to make use of cost-efficient and lightweight materials and components, such like plastic materials. In this regard, the injection device may comprise a large number of plastic components. It may even consist of plastic components, in particular of injection molded plastic components.

According to another embodiment the reservoir displacing arrangement and the needle displacing arrangement are separately connected with the pressure container. The separate coupling or separate connecting of reservoir displacing arrangement and needle displacing arrangement with the pressure container provides a rather direct force path between the pressure container and the reservoir displacing arrangement as well as between the pressure container and the needle displacing arrangement. By the separate connection the reservoir displacing arrangement may be triggered and operated rather independently of the needle displacing arrangement and vice versa.

By means of the separate connection it is also conceivable, that the process of needle displacing conducted by the needle displacing arrangement and the process of reservoir displacing conducted by the reservoir displacing arrangement at least partially overlap in time. In other words, a reservoir displacing arrangement may start at a time where a needle displacing is still in progress or vice versa. Additionally, it is conceivable, that reservoir displacing and needle displacing takes place substantially or almost simultaneously. In any case, by the separate connection or coupling of reservoir displacing arrangement and needle displacing arrangement with the pressure container, a multitude of different operation sequences or different injection steps are implementable.

The separate connection of the pressure container with the reservoir displacing arrangement and the needle displacing arrangement may also support and define a sequential activation and triggering of the injections device's functions and dispensing steps.

According to another embodiment the pressure container is sealed by an axially displaceable driving piston mechanically connected to a drive member of the needle displacing arrangement.

In this way, the needle displacing arrangement can be directly mechanically engaged with the driving piston of the pressure container. Expansion of the pressurized fluid may therefore immediately transfer to an axial displacement of the driving piston and hence to an activation of the needle displacing arrangement, thereby typically displacing the injection needle from the initial retracted position into the extended position.

While the needle displacing arrangement may be mechanically coupled to the driving piston of the pressure container the reservoir displacing arrangement may be pneumatically or hydraulically coupled to the pressure container. By means of a hydraulic or pneumatic coupling, the geometric arrangement of the reservoir displacing arrangement relative to the pressure container can be almost arbitrarily designed. Moreover, a hydraulic or pneumatic coupling between reservoir displacing arrangement and pressure container allows to arrange the pressure container and the reservoir displacing arrangement at a certain distance from each other. The volume of the housing and the construction space can therefore be optimized or minimized.

In an alternative embodiment it is also conceivable that the driving piston of the pressure container is mechanically connected to the reservoir displacing arrangement for displacing the medicament reservoir at least from an initial position to a dispensing position.

Irrespective on whether the driving piston of the pressure container is mechanically engaged to the needle displacing arrangement or to the reservoir displacing arrangement the driving piston is axially displaceable from an initial position at least into a first extended position and further into a second extended position under the effect of the pressurized fluid. When starting from an initial position and when the injection device is activated the driving piston is axially displaced from the initial position towards the first extended position. In the first extended position the driving piston may be blocked or stopped by a stop element, e.g. by a needle stopper.

The stop element may prohibit a further axial displacement of the driving piston past the first extended position. When the driving piston is connected to the drive member of the needle displacing arrangement also a needle displacing procedure will be blocked or stopped by the stop element engaging with the drive member or with the driving piston. By means of such a stop element, the driving piston and the drive member may rest in the first extended position, e.g. during the entire process of drug delivery. When drug delivery has terminated, the stop element may be retracted or displaced in order to release the driving piston and/or the drive member so that the driving piston can be further axially displaced from the first extended position towards the second extended position under the effect of the pressurized fluid.

In the present context, mechanical connection between the drive member and the driving piston means at least a one-directional or bidirectional thrust transferring coupling between the driving piston and the drive member. In this way, an axial displacement of the driving piston is unalterably transferable to a respective axial displacement of the drive member of the needle displacing arrangement. The mechanical connection between the driving piston and the drive member may also include a hinge- or lever arrangement to modify driving forces and displacement amplitudes of the drive member of the needle displacing arrangement. By means of a hinge- and/or lever arrangement, also the direction of the displacement of the drive member may be arbitrarily modified in comparison to the axial displacement of the driving piston.

Driving piston and drive member may be displaceable in a parallel way. The driving piston and drive member may be provided as two separate but mutually interconnected components. Alternatively, the driving piston and the drive member may be integrally formed. Hence, the driving piston sealing the pressure container may form a sealing portion of the drive member of the needle displacing arrangement. In this way, a rather direct mutual mechanical coupling between the pressure container and the needle displacing arrangement can be provided.

According to another embodiment the drive member comprises at least one sliding block guide portion at least in sections extending at a predefined angle with respect to the drive member's displacement direction the axial direction. The sliding block guide portion is further engaged with a needle tappet engaged with and/or connected to the injection needle. The needle tappet may extend at a predefined angle with respect to the elongation of the injection needle. The needle tappet may for instance extend substantially perpendicular to the elongation of the injection needle. Typically, the sliding block guide portion at least in sections extends at a predefined angle with respect to the drive member's displacement direction.

If integrally formed with the driving piston, a section of the sliding block guide portion extends at a predefined angle with respect to the axial direction. Otherwise, if the drive member is displaced by the driving piston along a direction different than the axial direction, the sliding block guide portion of the drive member extends at a predefined angle with respect to the drive member's displacement direction. Typically, the drive member is slidingly supported on and/or relative to the base between an initial position, a first extended position and a second extended position. Furthermore, the drive member is linearly and translationally displaceably mounted on the base. The drive member may be constrained and guided by a guiding structure having a hollow cross-section that mates with the outer circumference of the drive member.

Typically, the guiding structure and the drive member comprise a non-circular, for instance a keyed or cross-like shaped cross-section so that the drive member is rotatably locked to the guiding structure. In this way, the drive member may be exclusively translationally displaceable relative to the guiding structure and/or relative to the base along a predefined displacement direction, e.g. along the axial direction.

Since the drive member is for instance radially or tangentially constrained by a guiding structure it may be only displaced in axial direction. Since its sliding block guide portion at least in sections extends at a predefined angle with respect to the axial direction or with respect to the drive member's displacement direction, the needle tappet, which is e.g. axially constrained by the same or by a further guiding structure will experience a displacement in accordance to the slope of the sliding block guide portion. If for instance the sliding block guide portion extends at an angle of 45° in vertical direction with respect to the axial or horizontal direction, the needle tappet will experience a vertically-directed displacement when the drive member is displaced, e.g. from its initial position to its first extended position.

Since the needle tappet is mechanically engaged or mechanically connected with the injection needle, the pressure-induced displacement of the drive member from its initial position into its first extended position will trigger an extension and displacement of the injection needle out of the housing and/or beyond an outer contour or outer surface of the base. The base may for instance comprise a through opening, through which the injection needle may extend. The injection needle may be guided in or through said through opening. It may be further displaced along said through opening between the retracted and extended position.

By means of the mutual engagement of the needle tappet with the sliding block guide portion of the drive member, the direction of displacement of the needle may be redirected or deflected in comparison to the displacement direction of the drive member and/or of the axial displacement of the pressure container's driving piston.

According to the geometry of the sliding block guide portion provided in or on the drive member as a longitudinal or slanted groove, the injection needle displacement can be easily controlled and synchronized by and with the displacement of the drive member. Depending on the geometry and slope of the sliding block guide portion it is conceivable, that a further displacement of the drive member, e.g. beyond the first extended position is substantially effectless on the position of the needle tappet and/or on the position of the injection needle. Moreover, by inverting the direction or orientation of the sliding block guide portion in a different section, an oppositely directed displacement of the needle tappet can be generally triggered and conducted as the drive member is moved any further under the effect of the pressurized fluid.

Therefore and according to another embodiment, the injection needle is displaceable from the retracted position into the extended position by way of an axial displacement of the driving piston from an initial position to the first extended position. Typically, the axial displacement of the driving piston from the initial position to the first extended position is transferred to a corresponding displacement of the drive member from an initial position to a first extended position. Via the mutual engagement of the needle tappet and the sliding block guide portion, the injection needle is then displaced from the retracted position into the extended position.

According to a further embodiment the injection needle is displaceable from the extended position into the retracted position by way of an axial displacement of the driving piston from the first extended position to the second extended position. This displacing behavior is particularly implementable by providing a sliding block guide portion in or on the drive member having a first section extending at a predefined angle with respect to the drive member's displacement direction and having a second section extending at a different angle, typically at an inverted or opposite angle with respect to the drive member's displacement direction.

In this way, the displacement of the needle tappet during the displacement of the driving piston from the initial position to the first extended position can be substantially inverted when the driving piston is displaced further from the first extended position to the second extended position. In this way, a unidirectional and continuous axial displacement of the driving piston from the initial position to the second extended position is transferable into a forth and back movement of the injection needle, for the purpose of extending and retracting the injection needle prior to and after termination of a medicament delivery procedure.

According to another embodiment the pressure container comprises a first outlet in fluid communication with the reservoir displacing arrangement. The first outlet is sealed by the driving piston when the driving piston is in its initial position. The first outlet is at least partially in fluid communication with the pressurized gas of the pressure container when the driving piston is in the first extended position. Hence, by means of displacing the driving piston from the initial position into the first extended position the fluid communication between the first outlet and the pressurized gas is established. Typically, the pressurized gas tends to expand and to displace the driving piston in axial direction from its initial position towards its first extended position. Thereby the driving piston at least partially unveils the first outlet so that the pressurized gas flows through the first outlet towards the reservoir displacing arrangement. The first outlet of the pressure container is typically connected to the reservoir displacing arrangement via a fluid transferring connection, e.g. provided by a tube or by a channel.

The first outlet may be provided in a sidewall portion of the pressure container. The pressure container may comprise a tubular housing or a tubular-shaped barrel sealed by a disc-shaped driving piston extending all over the inner diameter of the pressure container. Along its outer circumference the driving piston typically comprises a sealing portion, e.g. a sealing surface tightly engaging with the inside-facing sidewall portion of the pressure container. In the initial configuration, the driving piston may coincide or substantially overlap with the first outlet of the pressure container. Alternatively it is conceivable, that the first outlet is located at a side of the initially positioned driving piston that faces away from the pressurized fluid. It is only upon expansion of the pressurized fluid that the driving piston is displaced in distal direction until the first outlet is at least partially unveiled to receive and to transfer the pressurized fluid towards the reservoir displacing arrangement.

In another embodiment the injection device comprises at least one throttle arranged in a flow path between the pressure container and the medicament reservoir to control a rate of medicament dispensing. The throttle may be arranged in a channel extending between the first outlet of the pressure container and the reservoir displacing arrangement. The type of throttle determines an influx of the pressurized fluid into the reservoir displacing arrangement and thereby determines the rate at which a driving pressure builds up that serves to displace the reservoir piston.

The specific design of the throttle in combination with the pressure level inside the pressure container and in combination with an immanent mechanical resistance of the medicament reservoir determines the velocity of the reservoir piston's axial displacement and hence the rate at which the medicament is expelled from the medicament container during medicament dispensing. The mechanical resistance of the medicament reservoir may result from friction forces between the reservoir piston and a sidewall of the medicament reservoir.

According to a further embodiment the reservoir displacing arrangement of the injection device comprises a stop member to limit a displacement of the medicament reservoir relative to the base. The reservoir displacing arrangement further comprises a driving unit hydraulically or pneumatically coupleable with the pressure container and comprising a driving chamber to slidably receive a proximal portion of the medicament reservoir. The driving chamber comprises inner dimensions and an inner contour that matches with the outer dimensions of the proximal portion of the medicament reservoir. The proximal portion of the medicament reservoir is therefore slidably displaceable inside the driving chamber. The driving chamber is furthermore in fluid communication with the first outlet of the pressure container.

Moreover, the medicament reservoir effectively seals the driving chamber in a distal direction so that an influx of the pressurized fluid in the driving chamber leads to a pressure build up inside said chamber. Since the medicament reservoir is slidably displaced in the driving chamber the rise of the fluid pressure in the driving chamber leads to a distally-directed displacement of the medicament reservoir relative to the driving chamber and hence relative to the driving unit until the distally-directed movement of the medicament reservoir is stopped by the stop member.

Typically, a distal end portion of the medicament reservoir abuts with the stop member thereby limiting the distally-directed and pressurized fluid-induced displacement of the medicament reservoir. The driving chamber also features a substantially cylindrical geometry and is open in distal direction to receive the correspondingly-shaped medicament reservoir. Hence, the medicament reservoir is typically also of cylindrical or tubular geometry. It is displaceable in the driving chamber in a sealed manner. For this, the inside-facing sidewall of the driving chamber comprises a seal to inhibit leakage of inflowing pressurized fluid. The driving chamber typically comprises a bottom portion featuring at least an inlet in fluid communication with the first outlet of the pressure container.

Said inlet and the pressure container's first outlet are typically connected by some kind of fluid transferring structure, such like a tube or a respective channel. In this way, a sequential or at least partially overlapping displacement of the injection needle and the medicament reservoir can be implemented. While displacing the driving piston in a first step towards its first extended position, the injection needle is displaceable into the extended position. When reaching the first extended position the driving piston at least partially unveils the first pressure container's outlet, thereby establishing a fluid communication between the pressurized fluid in the pressure container with the driving chamber of the driving unit. As a consequence, the medicament reservoir may then be pushed in distal direction towards the stop member in order to deploy and to initialize liquid medicament dispensing.

The triggering of the medicament reservoir displacing can be easily modified by the specific design and position of the first outlet of the pressure container. The axial position of the outlet in relation to the size of the driving piston determines the particular device configuration at which a medicament reservoir displacement starts.

According to another embodiment the stop member of the reservoir displacing arrangement comprises a tipped piercing member to penetrate a distal outlet of the medicament reservoir. The tipped piercing member typically extends in proximal direction, i.e. towards the medicament reservoir approaching the stop member. The piercing member is furthermore in fluid communication with the injection needle. Typically, injection needle and piercing member are in fluid communication by means of a flexible tube which allows that the injection needle is displaced relative to the stop member and/or relative to the piercing member rigidly attached thereto.

By means of a flexible fluid transferring connection between the piercing member and the injection needle, the piercing member can be fixed to the base. In this way, the number of moveable components of the injection device can be further reduced. The distal outlet of the medicament reservoir is typically provided with a pierceable sealing disc, such like a septum made of a natural or synthetic rubber. When reaching the dispensing position, the medicament reservoir typically abuts with its distal outlet end with the stop member in such a way, that the tipped piercing member of the stop member penetrates the medicament reservoir's distal outlet.

When reaching the dispensing position, hence when engaging with the stop member the proximal end of the medicament reservoir is still engaged with the driving chamber of the driving unit. By piercing the distal outlet of the medicament reservoir, a fluid pressure still present in the driving chamber may then serve to displace a proximal piston of the medicament reservoir in distal direction, thereby expelling the liquid medicament via the piercing member. Typically, the medicament reservoir comprises a cartridge featuring a rigid tubular or cylindrically-shaped barrel sealed in proximal direction by means of a piston slidably disposed therein. By exerting distally-directed pressure to the piston or by establishing a predefined pressure in the driving chamber, the proximally located piston is urged in distal direction, thereby expelling the liquid medicament from the cartridge.

Accordingly and following a further embodiment, the medicament reservoir comprises a rigid body proximally sealed by a reservoir piston. The reservoir piston is displaceable in a medicament dispensing direction, typically in distal direction, by way of the pressurized fluid flowing into the driving chamber of the reservoir displacing arrangement's driving unit. In this way, the reservoir displacing arrangement is not only adapted to displace the entire medicament reservoir but also to dispense the medicament from the medicament reservoir. The influx of the pressurized fluid into the driving chamber initially leads to a distally-directed displacement of the medicament reservoir until its distal outlet hits the stop member.

Friction forces acting between the inner sidewall of the driving chamber and the outer sidewall of the medicament reservoir are substantially lower than the friction forces acting between the reservoir piston and the rigid body of the medicament reservoir. In this way, a sequential displacement of the medicament reservoir as a whole relative to the base and a subsequent displacement of the piston relative to the displaced medicament reservoir can be provided. Moreover, as long as the distal outlet of the medicament reservoir is not yet penetrated by the piercing member the reservoir piston is almost not displaceable in dispensing direction due to the substantial incompressibility of the medicament located in the medicament reservoir.

Alternatively, the medicament reservoir comprises a flexible bag that proximally sealed by a flexible membrane, which is displaceable in a medicament dispensing direction by way of the pressurized fluid flowing into the driving chamber of the reservoir displacing arrangement's driving unit. By applying pressure to and into the driving chamber the reservoir's flexible membrane extends into interior of the reservoir thereby applying a fluid pressure to the fluid container in the reservoir in order to expel the same from the reservoir.

According to another embodiment the injection device further comprises a locking member extending with a shaft portion through or into the needle displacing arrangement to block a displacement of the pressure container's driving piston in its initial position. Typically, the shaft portion of the locking member is adapted to block a distally-directed and pressurized fluid-induced displacement of the pressure container's driving piston. For this the shaft portion may directly engage with the drive member of the needle displacing arrangement. Since the drive member is mechanically connected with the driving piston, a blocking or locking of the drive member in its initial position also blocks or locks the driving piston in its initial position.

It is only upon removal of the locking member and its shaft portion from the needle displacing arrangement, that a distally directed displacement of the driving piston is no longer blocked or prevented so that removal of the shaft portion from the needle displacing arrangement actually liberates a distally directed displacement of the driving piston under the action of the expanding pressurized fluid. The locking member typically comprises a ring portion to be gripped by at least one finger of a patient's hand. In this way, the locking member can be easily gripped and removed from the needle displacing arrangement in a rather intuitive way.

With the locking member blocking a distally-directed displacement of the pressure container's driving piston, the sequence of various dispensing steps can be triggered and initialized simply by removing the locking member. In this way, activation of the injection mechanism of the injection device only requires removal of the locking member. As soon as the locking member is removed or displaced in such a way that its shaft portion liberates the needle displacing arrangement, the driving piston is immediately pushed in distal direction under the action of the pressurized fluid, thereby inducing a displacement of the injection needle towards its extended position.

In addition and according to a further embodiment, the injection device comprises a safeguard member removably attached to the base and releasably and/or frangibly connected to the locking member. The safeguard member serves to inhibit a premature or unintentional removal of the locking member. In an initial configuration of the injection device, the locking member and the safeguard member are connected. The connection of the locking member and the safeguard member may comprise a predetermined breaking structure or a structurally weakened portion, which disintegrates or breaks as soon as a force above a predefined threshold acts on the locking member to remove the same from the needle displacing arrangement. In addition or alternatively, the safeguard member and the locking member may also be positively and/or frictionally engaged.

The safeguard member may extend into the base but may also comprise a portion extending from the base of the injection device, such like a gripping tab, in order to grip and to remove the safeguard member. Upon grasping and removing the gripping tab, the connection between the safeguard member and the locking member can be abrogated. In an embodiment it is also conceivable, that the safeguard member is covered or is integrated into a protective foil covering an application area of the injection device, e.g. a lower side of the base which is intended to get in direct contact with the patient's skin for the purpose of medicament injection.

It is conceivable, that the safeguard member is only accessible after the protective foil has been removed or that the safeguard member is removed together with the protective foil, e.g. when the safeguard member is integrated into said foil. It is also conceivable, that the safeguard member at least partially protrudes from the outer contour of the base and that the safeguard member is covered by the protective foil. By gripping and lifting of the protruding portion of the safeguard member, e.g. the gripping tab, also the protective foil may be lifted and removed in a rather convenient and self-explaining way from the lower side of the base.

According to another embodiment the injection device further comprises a retraction arrangement mechanically engaged with a needle stopper to displace the needle stopper into a release position, in which the driving piston is displaceable into the second extended position. The retraction arrangement may be also driven by the pressurized fluid typically after the dispensing action of the liquid medicament has terminated. By means of the retraction arrangement, the needle stopper, that serves to limit the axial displacement of the driving piston when reaching the first extended configuration, is displaceable into a release position, in which the drive member and hence the driving piston of the pressure container is or are liberated for a further displacement in distal direction under the action of the pressurized fluid.

In an initial configuration the needle stopper serves to stop and to limit the distally-directed displacement of the driving piston so that displacement of the medicament reservoir and a subsequent dispensing action may take place. When the dispensing action terminates, i.e. when the reservoir piston reaches a distal end position, in which almost the entirety of the liquid medicament has been expelled from the medicament reservoir, the retraction arrangement is triggered to displace the needle stopper into the release position. Triggering of the retraction arrangement may occur in different ways.

In a further embodiment the retraction arrangement comprises a barrel sealed by a displaceable release piston operably engageable with the needle stopper. Furthermore, the barrel comprises an inlet in fluid communication with a discharge outlet of the reservoir displacing arrangement. The discharge outlet may be sealed by a plug or by a respective seal being connected or mechanically coupled with the reservoir piston of the medicament reservoir. In this way, the plug or seal may automatically remove and may thus liberate the discharge outlet as soon as the reservoir piston reaches its distal end position in the medicament reservoir. In this way, the pressurized fluid present in the driving chamber may emanate the chamber and may flow into the retraction arrangement's barrel thereby displacing the release piston and to displace the needle stopper into the release position.

Alternative to a direct mechanical engagement between the reservoir piston and a plug sealing the discharge outlet it is also conceivable to provide a kind of pressure-sensitive valve, such like a check valve in the driving chamber of the driving unit or elsewhere in the fluid flow paths of the injection device. The pressure-sensitive valve may be closed below a predefined pressure, which is typically larger than the pressure level at which medicament delivery takes place. As soon as the system pressure rises above a given pressure threshold the pressure-sensitive valve of the driving chamber opens and establishes the fluid communication between the driving chamber and the retraction arrangement.

According to another alternative, the reservoir piston may be directly or indirectly mechanically engaged with the needle stopper, e.g. by way of a tensile- or pressure transferring interconnection. For instance, the reservoir piston may be connected with one end of a rope extending through a proximal seal of the medicament reservoir and/or through a seal of the driving chamber. An opposite end of the rope or cable pull may be further operably engaged with the needle stopper to displace the latter into the release position when the reservoir piston arrives at a predetermined end position or stop position. The rope or cable may be guided and deflected by means of a pulley or deflection roller to support an almost arbitrary geometric arrangement of the needle stopper relative to the medicament reservoir.

Implementation of a pressure-sensitive valve is of particular benefit when the pressure of the pressurized fluid inside the pressure container is much larger than the operating pressure at which displacement of the reservoir piston relative to the rigid body of the reservoir takes place. Typically, at least one throttle is provided in the flow path between the driving chamber and the first outlet of the pressure container. In this way, the fluid pressure in the driving chamber constantly rises over time until the pressure in the driving chamber approaches the pressure of the pressurized fluid in the pressure container.

Making use of a throttle is also of particular benefit for the dispensing of the liquid medicament. Due to inevitable manufacturing and assembly tolerances the elastic reservoir piston may experience varying friction forces as it is displaced in the rigid body of the medicament reservoir. If, for instance a continuous displacement of the reservoir piston is interrupted said piston may have experienced a local increasing friction with regard to the rigid body. Consequently, movement of the reservoir piston may stop.

As a consequence, the constant influx of the pressurized fluid into the driving chamber leads to a pressure increase up to a level which is high enough to overcome the increased friction effect and to displace the reservoir piston further in distal direction. Such a displacement also comes along with an increasing volume of the driving chamber so that the fluid pressure decreases to a normal level. Making use of a compressible fluid provided by the pressure container allows to effectively compensate any varying friction effects of the reservoir piston relative to the rigid body of the medicament reservoir.

According to another embodiment the pressure container comprises a second outlet in fluid communication with a signal generator. The second outlet is at least partially in fluid communication with the pressurized fluid when the driving piston is in the second extended position. The second outlet is typically axially separated from the first outlet of the pressure container. The second outlet of the pressure container typically acts as a relief opening. It is typically in fluid communication with a whistle so as to generate an audible sound at the end of a dispensing procedure. Typically, after the needle stopper has been displaced into the release position the drive member and the driving piston are liberated to move further towards the second extended position.

During this displacement the injection needle is typically retracted into its initial position so that its tipped end portion does no longer protrude from the base or from a housing of the injection device. When the injection needle reaches the retracted position after termination of a dispensing procedure the driving piston reaches the second extended position, in which the second outlet is at least partially in fluid communication with the pressurized fluid so that the pressurized fluid may escape via the signal generator.

In addition or alternative to the signal generator embodiment it is also conceivable that the drive member protrudes from the housing or from the base of the injection device when reaching the second extended position. In this way, a tactile feedback can be provided to a user that medicament delivery has terminated.

The pressure container is typically filled with a pressurized gas. Suitable propellant gases provided by the pressure container are selected from: butane, dimethylether or propane. The pressure container can comprise a conventional cartridge design with an inner volume in the region of 3 ml and further having a driving piston with a surface below 300 mm$^2$. Given a butane vapor pressure of around 2 bar a maximum force of around 60 Newton can be obtained. Making use of dimethyl ether at a pressure of 5.1 bar, a maximum force of 145 Newton can be obtained. By making use of propane at a pressure of 8.3 bar, a maximum force above 200 Newton, for instance 235 Newton can be obtained.

Ignition temperatures of the mentioned propellant gases are above 170° C. so that the pressure container may be preassembled in the injection device together with the medicament reservoir. Thereafter, the injection device with the preassembled pressure container may become subject to a heat treatment, for instance for sterilization purpose. Moreover, the ignition point is above a melting temperature of various thermoplastic materials, such like polypropylene or polyethylene. In this way, the pressure container can be filled with a gas and may be subsequently sealed by means of a molding process. Additionally, the mentioned propellants provide a rather constant pressure and force effect even when emanating the pressure container.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser -Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(02)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, various embodiments of the invention will be described by making reference to the drawings, in which:

FIG. 26a is illustrative of an alternative fluid transferring coupling of the pressure container with the driving chamber making use of an additional check valve and FIG. 26b shows another force-displacement diagram obtained with the configuration according to FIG. 26a.

DETAILED DESCRIPTION

Figure 1:
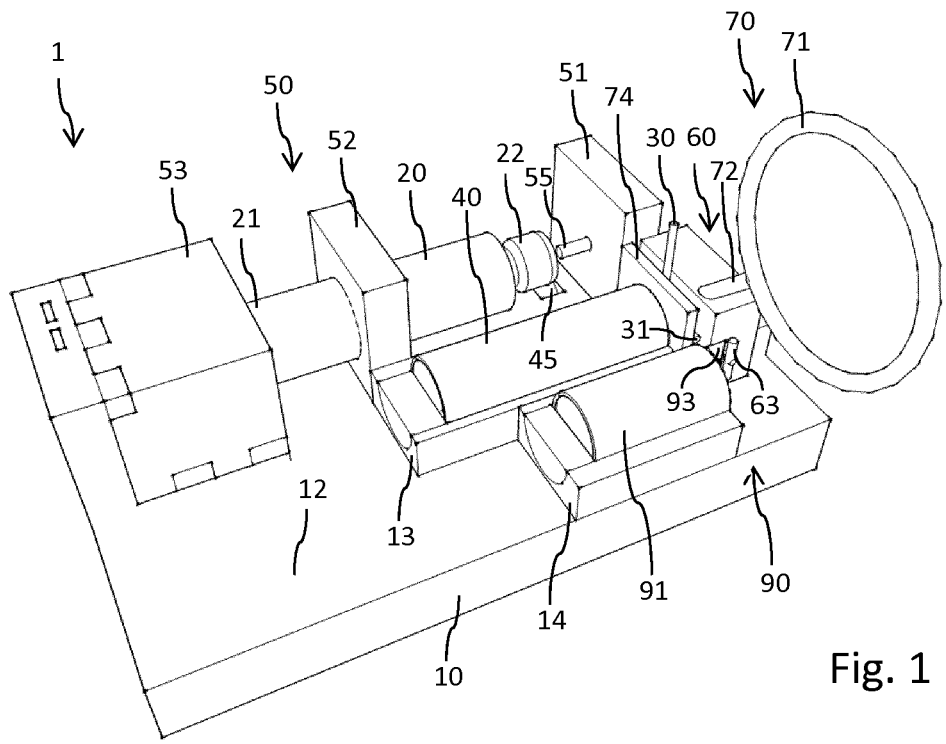
FIG. 1 shows a perspective illustration of the injection device in an initial configuration.

As illustrated in FIG. 1 the injection device 1 comprises a planar-shaped base 10 that serves as a mounting platform for the various components of the injection device 1. The injection device comprises a displaceable medicament reservoir 20, which in the present embodiment comprises a rigid cartridge with a sealed distal outlet 22 and with a oppositely located proximal portion 21 slidingly arranged in a driving unit 53 of a reservoir displacing arrangement 50.

Additionally, the injection device comprises a pressure container 40 that is fixed to the base 10. Like the medicament reservoir 20 also the pressure container 40 comprises a tubular or cylindrical shape. The pressure container 40 typically comprises a cylindrically-shaped barrel having a plug 47 at one end and featuring a displaceable driving piston 41 at the opposite end. The driving piston 41 sealing the inner volume of the barrel 44 is displaceable inside the barrel 44 along the longitudinal direction thereof. The driving piston 41 is mechanically engaged or is directly connected to a drive member 61 of a needle displacing arrangement 60.

Figure 5:
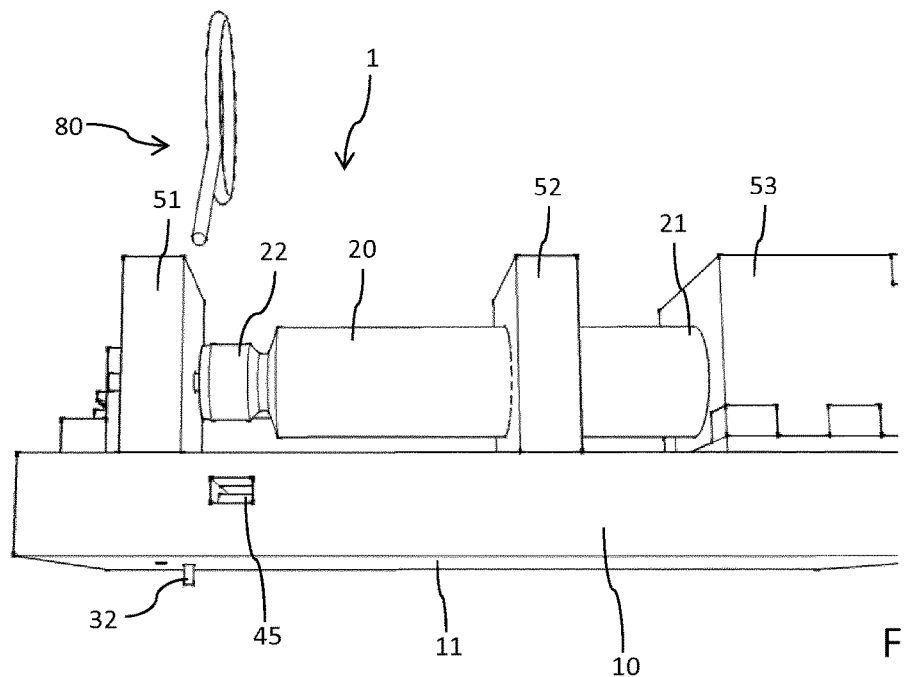
FIG. 5 is a sideview of the injection device with extended injection needle and with the medicament reservoir in a dispensing position.

As can be seen in FIG. 1, an injection needle 30 extends substantially perpendicular to the plane of the base 10. By activating the needle displacing arrangement 60 the needle 30 is to be displaced from an initial position as illustrated in FIG. 1 into an extended position as shown in FIG. 5, in which a dispensing end 32 of the injection needle 30 extends through and from the lower surface 11 of the base 10. There is further provided a retraction arrangement 90 comprising a barrel 91 and a plug 95 at a proximal end facing away from the needle displacing arrangement 60. The opposite end of the barrel 91 is sealed with a displaceable piston 92 which is connected with a release member 93. The release member 93 is in turn operably engageable with a needle stopper 63. As will be explained below, displacement of the release piston drives the needle stopper 63 into a release position 63b in order to liberate a displacement of the drive member 61 into a second extended position 61c, as for instance indicated in FIG. 6.

Figure 2:
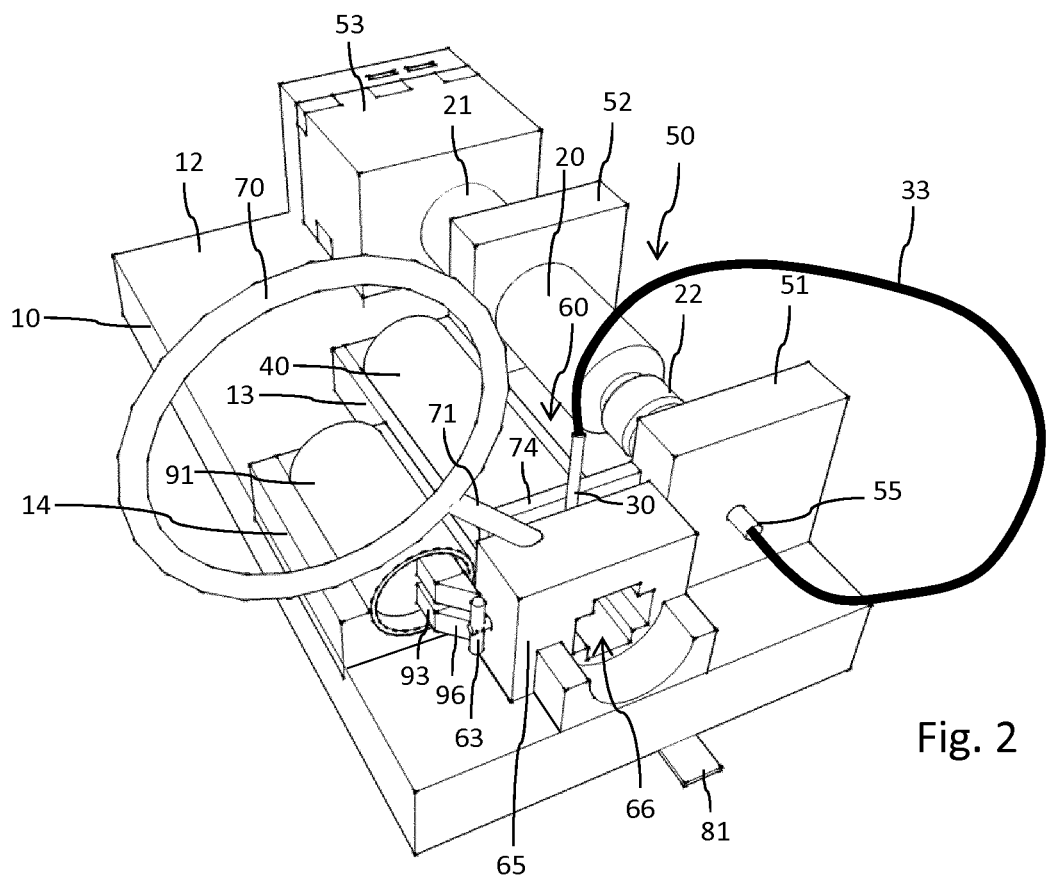
FIG. 2 shows the injection device as seen from another perspective.
Figure 3:
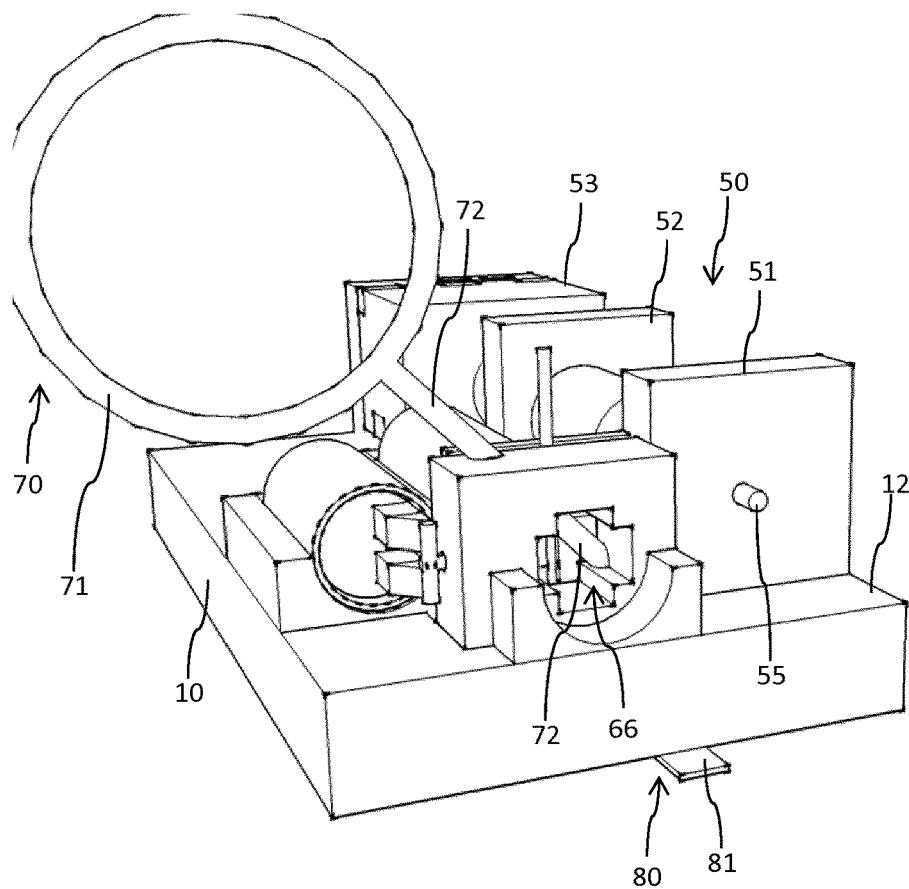
FIG. 3 is another perspective view of the injection device according to FIGS. 1 and 2.
Figure 4:
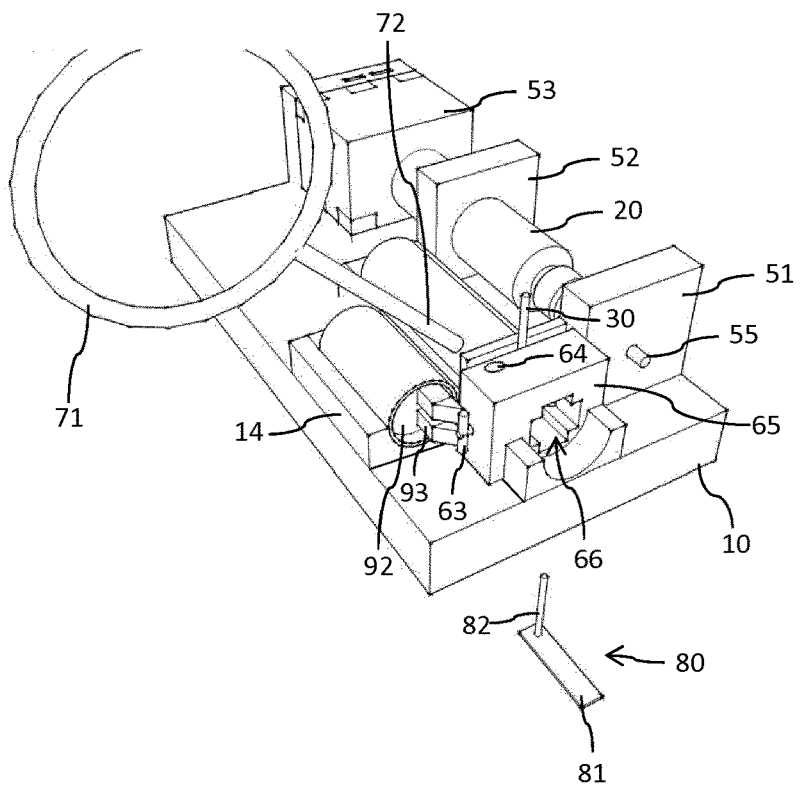
FIG. 4 shows the injection device with a removed safeguard member and removed lock member.

In the following, the operation of the injection device 1 will be described. In an initial configuration as shown in FIGS. 1-3 a lock member 70 extends into or even through the needle displacing arrangement 60. The lock member 70 comprises a ring portion 71 and a radially outwardly extending shaft portion 72. As shown in FIGS. 3 and 4, the shaft portion extends through a correspondingly-shaped slot 64 of a guiding structure 65 having a through opening 66 into and through which the drive member 61 may extend in the course of the dispensing procedure.

In the initial configuration the through opening 66 of the guiding structure 65 is traversed by the shaft portion 72 of the lock member 70, thereby blocking a displacement of the drive member 61 in longitudinal, hence in axial direction 2. In the present context, the axial direction refers to the tubular shape of the pressure container 40 and denotes the longitudinal axis thereof. As can be seen in the various Figures, the pressure container 40, the medicament reservoir 20 as well as the retraction arrangement 90 are arranged substantially parallel with respect to each other.

However, since the pressure container 40 is pneumatically or hydraulically coupled to the medicament reservoir 20 and to the retraction arrangement 90, the medicament reservoir 20 as well as the retraction arrangement 90 may be arranged in a different orientation compared to the longitudinal direction of the pressure container 40. For this the term "axial direction" or "axial displacement" as used herein generally refers to a longitudinal direction or longitudinal displacement in regard of a tubular barrel of different components or units of the injection device even when such barrels should not be oriented parallel to each other.

The guiding structure 65 may be integrally formed with the base 10. It extends upwardly from the upper planar surface 12 of the base 10. The pressure container 40 is fixed in a first frame 13 extending upwardly from the upper surface 12 of the base 10. In a similar way also the barrel 91 of the retraction arrangement 90 is fixed on the base 10 by means of a second frame at least partially surrounding the outer circumference of the barrel 91. Even though not illustrated the injection device 1 is typically provided with an outer housing covering most of the components of the injection device apart from the ring portion 71 of the lock member. The ring portion 71 at least partially extends out of the housing in order to enable gripping thereof by a user. In the initial configuration as for instance shown in FIG. 3, the lock member 70 extending into the needle displacing arrangement 60 and through or laterally across the through opening 66 may be frangibly or positively connected with a upwardly-extending shaft portion 82 of a safeguard member 80 as separately illustrated in FIG. 4.

The shaft portion 82 extends through a correspondingly-shaped orifice of the base 10. The shaft portion 82 is further connected with a gripping tab 81 extending along the lower surface 11 of the base 10 in the initial configuration as shown in FIG. 2. The safeguard member 80 may be adhesively connected to the lower surface 11 of the base 10. Since the safeguard member 80 is connected with the lock member 70 the safeguard member effectively prevents unintentional or premature release and withdrawal of the lock member 70. Additionally or alternatively, the safeguard member 80 may be connected or integrated into a protective foil covering the entire lower surface 11 of the base 10. Upon removal of the protective foil, which is not illustrated, the base 10 can be attached with its lower surface 11 to a skin portion of a patient.

Instead of a frangible connection of safeguard member 80 and lock member it is also conceivable, that safeguard member 80 and lock member 70 are positively engaged. Even though not illustrated, it is conceivable, that a free end of the lock member's 70 shaft portion 72 comprises an orifice to receive the upward pointing shaft portion 82 of the safeguard member 80. In this way, the safeguard member 80 may be easily withdrawn in vertical direction, i.e. perpendicular to the plane of the base 10, thereby liberating the lock member 70.

Figure 15:
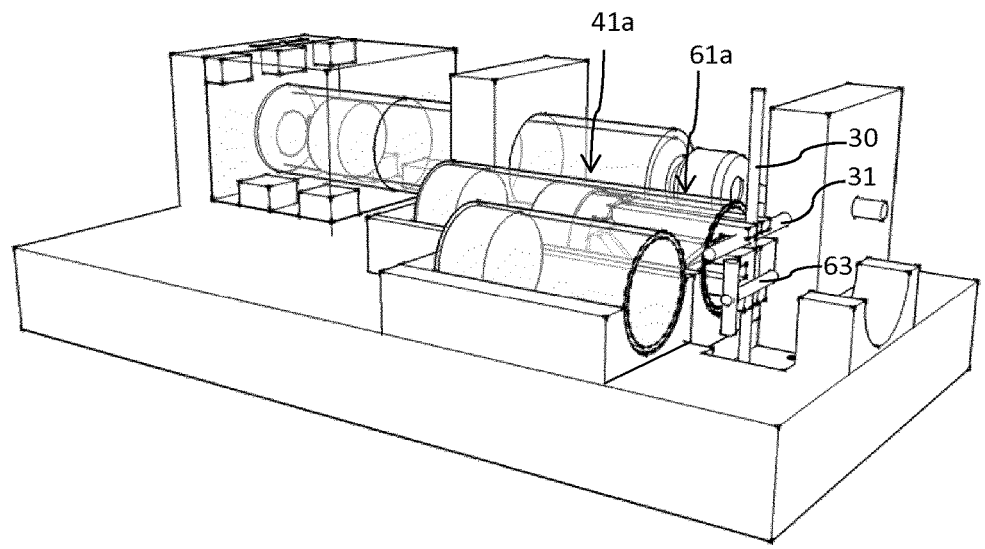
FIG. 15 is illustrative of the injection device with the drive member in an initial position.
Figure 16:
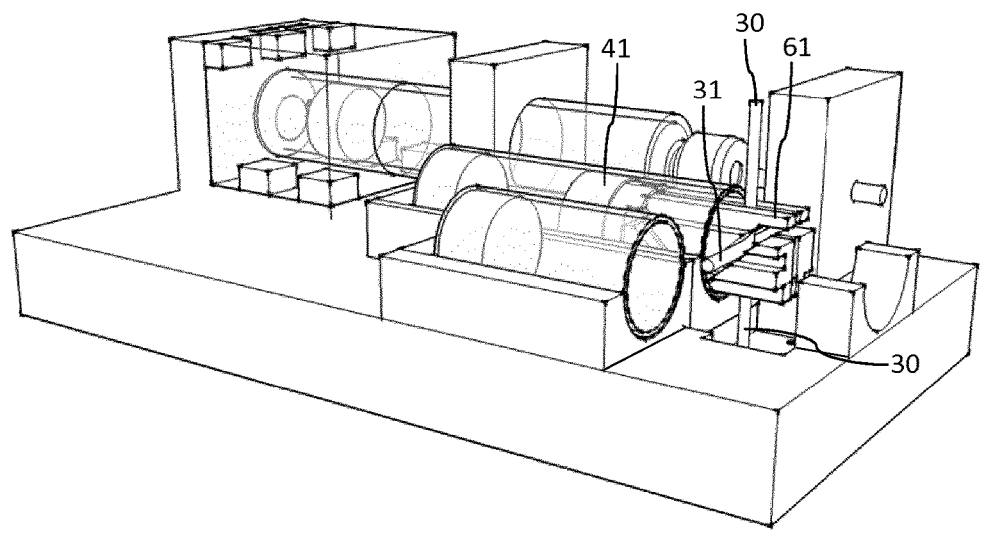
FIG. 16 shows the injection device with the drive member located between the initial position and the first extended position.
Figure 17:
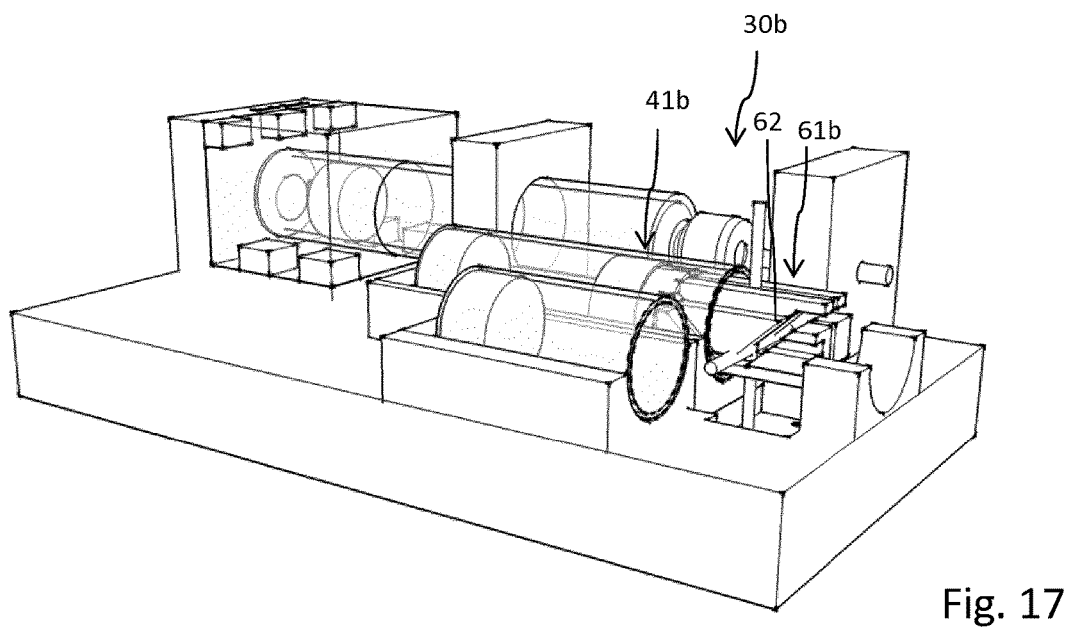
FIG. 17 shows the drive member in its first extended configuration.
Figure 18:
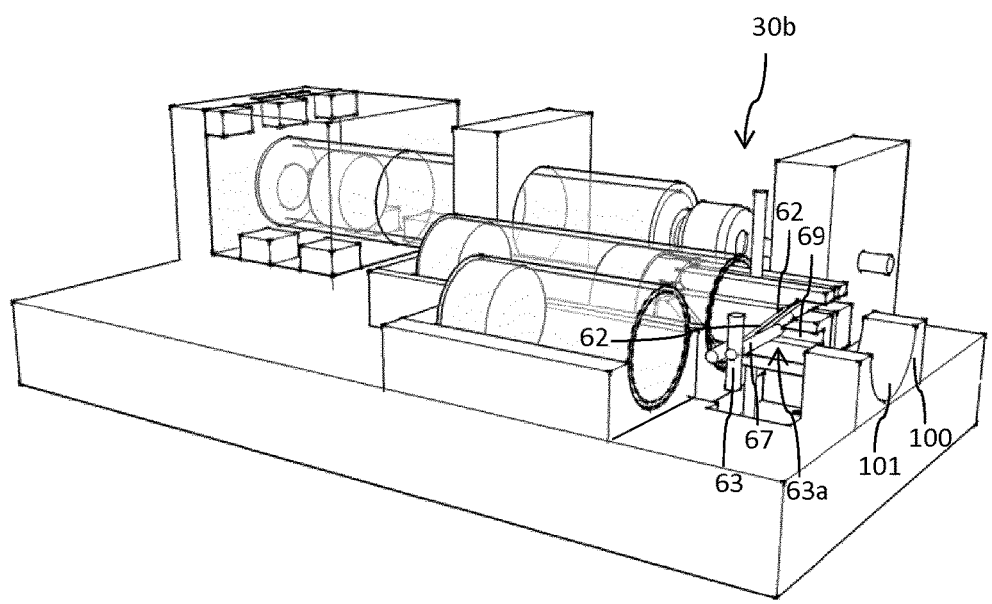
FIG. 18 shows the interaction of the drive member with a needle stopper when the drive member is in its first extended position.

Once the safeguard member 80 has been removed, the lock member 70 is to be withdrawn and to be removed from the through opening 66 and out of the needle displacing arrangement's 60 slot 64 as illustrated in FIG. 4. By removing the lock member 70 the drive member 61 as for instance shown in FIGS. 7-10 is displaceable from an initial position 61a as for instance indicated in FIG. 15 into a first extended position 61b as for instance shown in FIGS. 7-10 and 17. A further axially and distally-directed displacement of the drive member 61 is blocked by a needle stopper 63 extending into and through a lateral side portion of the guiding structure 65. The needle stopper 63 is separately illustrated in FIGS. 18 and 19. It comprises a T-shaped structure and has a locking pin 67 extending into the through opening 66 of the guiding structure 65 when in a stop position 63a as indicated in FIG. 18. In the stop position 63a as indicated in FIG. 18 the free end of the locking pin 67 engages and abuts with a sliding block guide portion 62a of the drive member 61.

Figure 19:
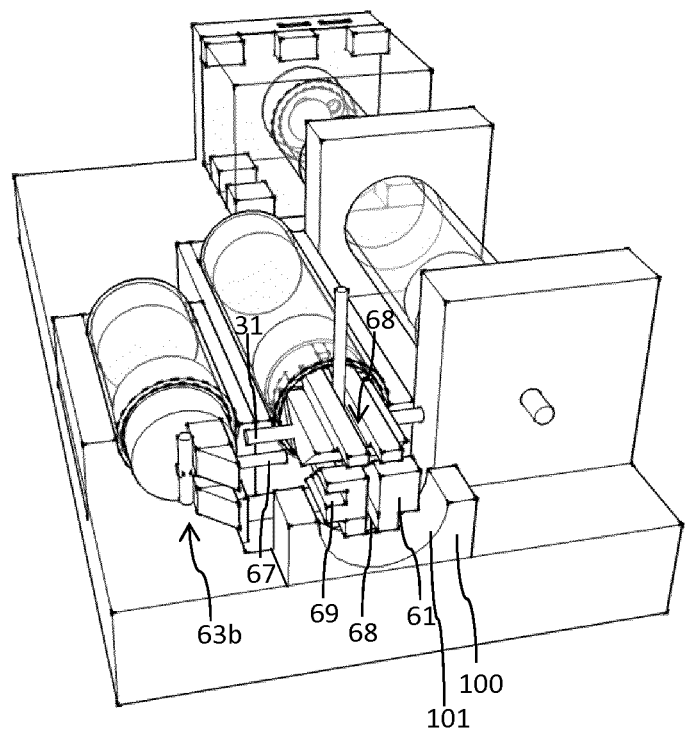
FIG. 19 shows the retraction arrangement in engagement with the needle stopper and FIG. 20 shows the drive member in its second extended position.

In this way, the needle stopper 63 limits a further axial displacement of the drive member 61 under the effect of the expanding pressurized fluid 24 located in the pressure container 40. A further displacement of the drive member 61 into its second extended position 61c requires that the needle stopper 63 is displaced from its stop position 63a as shown in FIG. 18 into a release position 63b as shown in FIG. 19. It is then that the needle stopper 63 liberates the drive member 61 so that the drive member 61 may be displaced further in axial direction 2 under the effect of the expanding pressurized fluid 24 until the drive member 61 reaches a second extended position as illustrated in FIG. 20.

Figure 20:
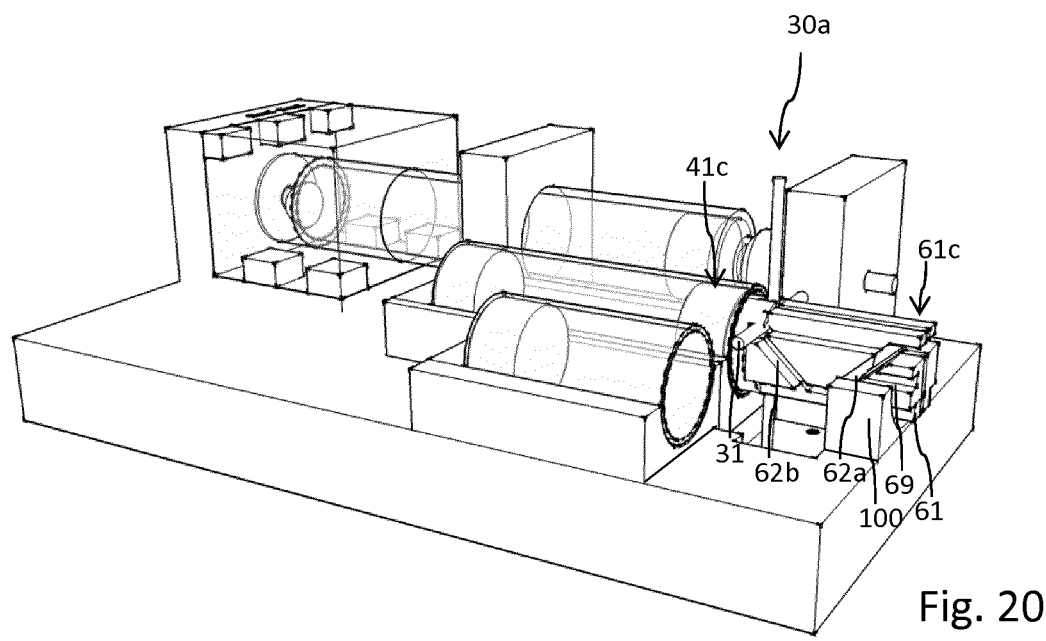

As further illustrated in FIG. 20 there is further a support 100 on the base 10 to receive and to mechanically support the drive member 61 when reaching the second extended position 61b. The support extends at the upper side 12 of the base and flushes with a lateral side of the base 10. Moreover, the support 100 comprises a curved or semi-circular support surface 101 to receive and to support the axially extended drive member 61. In this way the support 100 serves to prevent cant of the drive member 61 and/or of the driving piston 41 with the barrel 44 of the pressure container 40.

When the drive member 61 is initially displaced from its initial position 61a into the first extended position 61b the operable engagement between the drive member 61 and the injection needle 30 leads to displacement of the injection needle 30 towards its extended position 30b. As shown in detail in FIG. 14, the injection needle 30 extending substantially perpendicular to the plane of the base 10 is rigidly connected with a needle tappet 31 extending substantially parallel to the plane of the base 10. The drive member 61 comprises a vertical slot 68 through which the injection needle 30 extends. The vertical slot 68 substantially extends over the entire elongation of the drive member 61, hence in axial direction 2. In this way, the pressurized fluid driven axial displacement of the drive member 61 has no direct effect on the position of the injection needle 30.

The drive member 61 further comprises a sliding block guide portion 62 having a first section 62a and a second section 62b. First and second sections 62a, 62b are axially separated. Hence, first and second sections 62a, 62b are axially offset. The first and the second sections 62a, 62b extend at a certain angle relative to the axial direction 2, hence relative to the longitudinal direction of the drive member 61 or relative to the displacement direction of the drive member 61. The first section 62a of the sliding block guide portion 62, in which the needle tappet 31 is initially guided extends from a bottom portion of the drive member 61 towards an upper portion of the drive member 61 as seen in axial direction. Accordingly and when the drive member 61 is displaced from its initial position 61a into the first extended position 61b the needle tappet 31 experiences a downward-directed displacement, i.e. towards the base 10.

With this vertical displacement of the needle tappet 31 also the injection needle experiences a respective downwardly-directed displacement and reaches the extended position. The drive member 61 further comprises a horizontal slot 69 extending from a free end of the drive member 61 into the first section 62a of the sliding block guide portion 62.

This groove-shaped horizontal slot 69 is particularly adapted to receive the locking pin 67 of the needle stopper 63 as the drive member 61 is displaced from its initial position 61a into its first extended position 61b. In this way, the locking pin 67 of the needle stopper 63 may abut and engage with the sliding block guide portion 62 in order to limit an axial displacement of the drive member 61. Typically, the sliding block guide portion 62 and the needle stopper 63 are designed and positioned in such a way, that the pressurized liquid induced axial displacement of the drive member 61 just stops when the needle 30 has reached the extended position 30b.

As for instance illustrated in FIGS. 1 and 2, the injection needle 30 is axially sandwiched between a proximal sidewall of the guiding structure 65 and a fixing plate 74 fixedly attached to the base 10. In this way, the injection needle 30 together with its needle tappet 31 is axially constrained relative to the base 10. In this way, an axial displacement of the drive member 61 does not transfer to the injection needle 30.

As becomes further apparent from the geometric shape of the through opening 66 and the outer contour of the drive member 61, the drive member 61 is rotatably fixed in the through opening 66. In particular, the through opening comprises a cross-like cross-section that mates with a cross-like cross-section of the drive member 61. In this way, a rotation of the drive member 61 around its longitudinal axis can be effectively prevented.

Axial displacement of the drive member 61 is obtained by a corresponding axial displacement of the driving piston 41 sealing the barrel 44 of the pressure container 40 in axial distal direction 2. As shown for instance in FIGS. 7-10 the driving piston 41 is directly connected to the drive member 61. It is even conceivable, that drive member 61 and driving piston 41 are integrally formed, wherein the driving piston 41 is just equipped or provided with a sealing member to provide a fluid tight seal of the barrel 44. Upon removal of the lock member 70, the driving piston 41 is driven from an initial position 41a into the first extended position as shown in FIGS. 7-10.

In the first extended position 41b the driving piston 41 at least partially liberates a first outlet 42 provided in the sidewall of the barrel 44 of the pressure container 40. As indicated by dotted lines in FIG. 6 the first outlet 42 is in fluid connection with a first channel 15 provided in or on the base 10. The channel 15 extends towards and/or into the driving unit 53. As further indicated for instance in FIGS. 6 and 7 the first channel 15 is in fluid communication with an inlet 57 of the driving chamber 54.

When the driving piston 41 reaches the first extended position 41b the driving chamber 54 will get in fluid communication with the inner volume of the pressure container 40 and will therefore be exposed to the expanding pressurized fluid 24. The inlet 57 of the driving chamber 54 is provided in a proximal bottom portion 58 of the driving unit 53. The driving chamber 54 is open towards the axial distal direction 2 but is sealed by the proximal portion 21 of the medicament reservoir 20. Upon applying a fluid pressure to the driving chamber 54, the reservoir piston 23 as well as the medicament reservoir 20 itself become subject to a distally-directed displacement towards a stop member 51 of the reservoir displacing arrangement 50.

Figure 7:
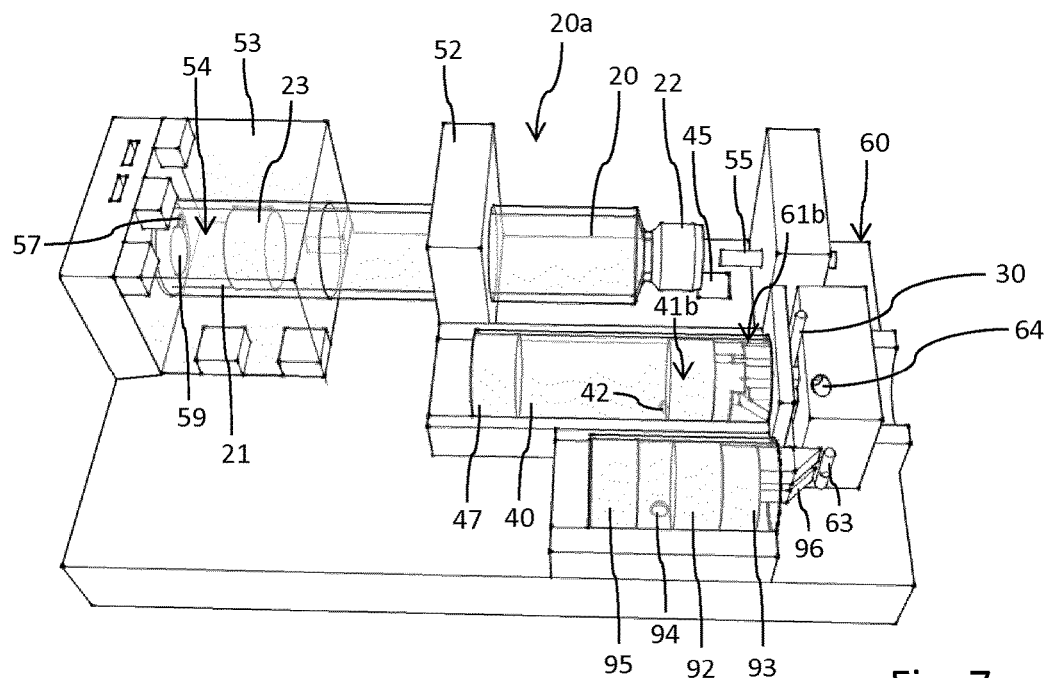
FIG. 7 shows the initial configuration of the injection device after removal of the lock member in a partially transparent illustration.
Figure 8:
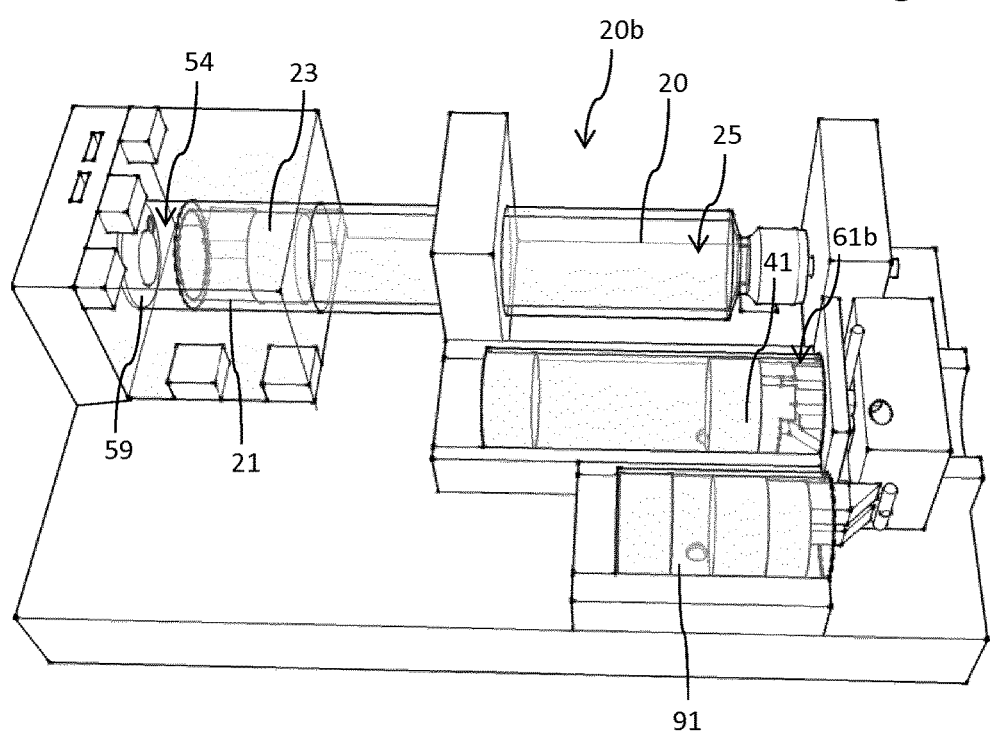
FIG. 8 shows the injection device with the medicament reservoir positioned in dispensing position.
Figure 9:
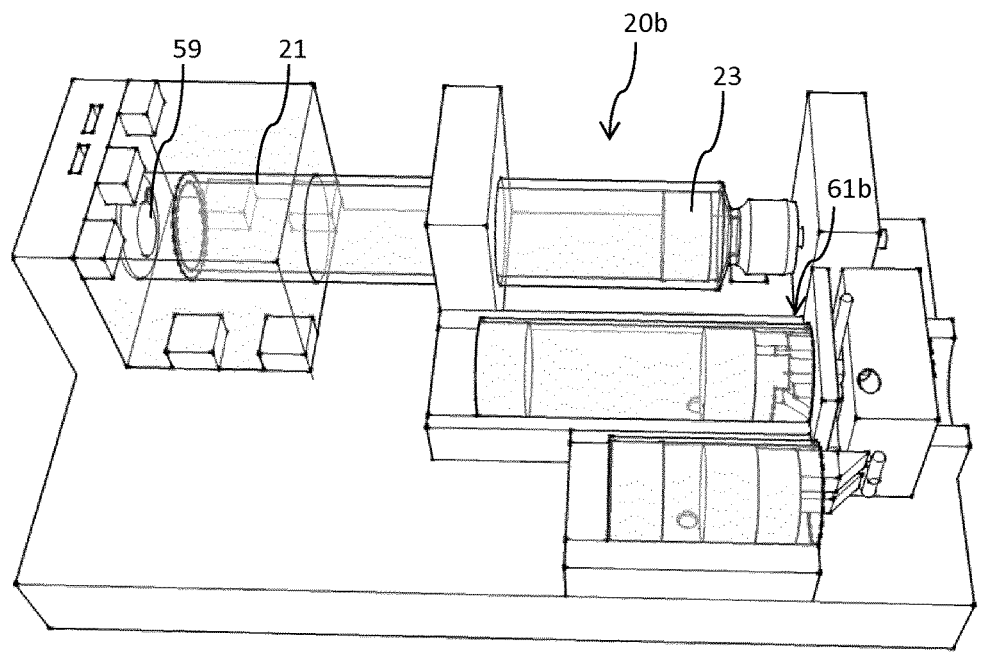
FIG. 9 shows the injection device wherein the reservoir piston has been displaced in distal direction towards the outlet of the cartridge.

The displacement of the entire medicament reservoir 20 from an initial position 20a to a dispensing position 20b is apparent from a comparison of FIGS. 7 and 8. When reaching the distal dispensing position 20b as indicated in FIG. 8, the distal outlet 22 of the medicament reservoir 20, typically comprising a pierceable septum, is penetrated and pierced by a tipped piercing member 55, thereby gaining access to the inner volume of the medicament reservoir 20. The displacement between the initial position 20a to the dispensing position 20b is further Supported and guided by a guiding member 52 arranged axially between the stop member 51 and the driving unit 53. The guiding member 52 comprises a through opening, in which the medicament reservoir 20 is radially supported and guided.

The opposite end of the piercing member 55 facing away from the medicament reservoir 20 is in fluid communication with the injection needle 30 by means of e.g. a flexible tube 33 as indicated for instance in FIG. 2. Making use of a flexible tube 33 to establish a fluid communication between the injection needle 30 and the piercing member 55 is beneficial in that the piercing member 55 can be fixed in an immobile way on or relative to the base 10 whereas the injection needle 30 is displaceable relative to the base between a retracted position 30a and an extended position 30b.

When reaching the dispensing position 20b, the medicament reservoir 20 gets in fluid communication with the injection needle 30 and a dispensing process may start. For delivery or dispensing of the liquid medicament nothing further has to be done. Typically, in the flow path between the pressure container 40 and the driving chamber 54 there is provided at least one throttle 46, as for instance indicated in FIG. 6. There, the throttle 46 is provided in the first channel 15 interconnecting the first outlet 42 of the pressure container 40 with the inlet 57 of the driving unit 53. By means of a throttle 46 a rather continuous and constant influx of pressurized fluid 24 into the driving chamber 54 can be provided. Given that the pressure container 40 represents a rather large source of energy, e.g. in form of a highly pressurized fluid, e.g. in form of a pressurized gas, the throttle 46 serves to limit influx into the driving chamber 54.

In this way, a rather constant and well-defined influx and a respectively rising fluid pressure can be established in the driving chamber 54. Since the medicament reservoir 20, in particular its distal outlet 22 is sealed as long as the medicament reservoir 20 is in its initial position 20*a*, any pressure applied to a proximal portion 21 of the medicament reservoir 20 leads to a distally-directed displacement of the medicament reservoir 20 relative to the base 10. As soon as the medicament reservoir 20 abuts with the stop member 51 and as soon as a liquid transferring flow communication between the medicament reservoir 20 and the injection needle 30 is established, the reservoir piston 23 sealing the proximal portion 21 of the medicament reservoir 20 can become subject to a distally-directed displacement relative to the barrel of the medicament reservoir 20, given that the fluid pressure inside the driving chamber 54 rises above a given threshold.

The dispensing rate or the flux of the liquid medicament can be governed and controlled by the design and type of the throttle 46, the type, the amount and the pressure of the pressurized fluid 24 provided in the pressure container 40.

Instead of or in addition to a separate throttle 46 it is also conceivable, that at least one of the first outlet 42 or the inlet 57 provides a respective throttle function, e.g. by having a rather small channel structure or diameter through which the pressurized fluid 24 may flow. It is generally conceivable, that the flow resistance of the flow path between the pressure container 40 and the driving unit 53 and/or its driving chamber 54 is designed and realized in such a way, that a well-defined throttle function is given for the pressurized fluid.

Figure 25A:
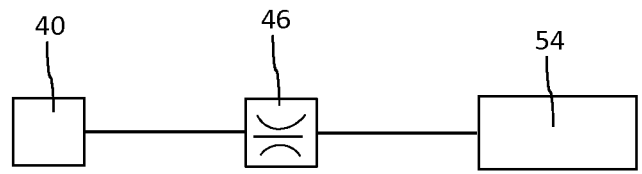
Figure 25B:
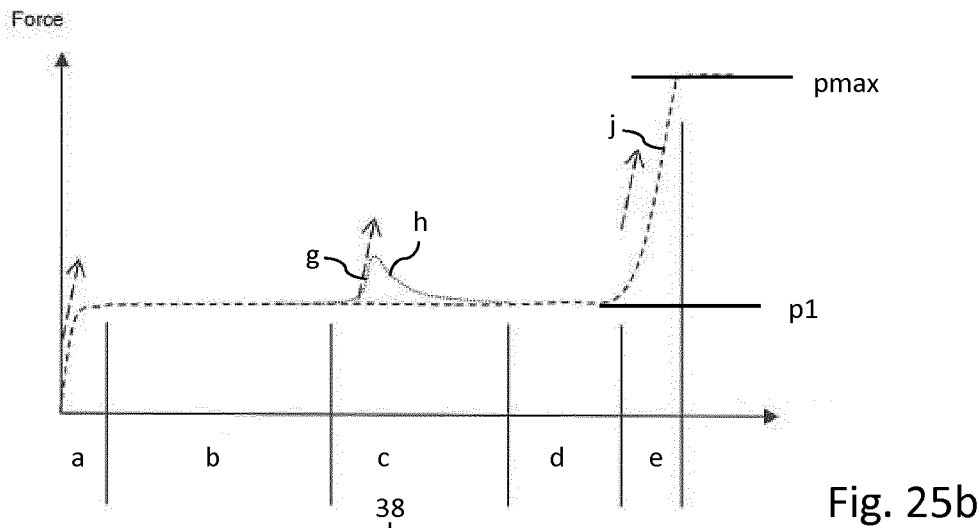

The flow resistance of the flow path between the pressure container 40 and the driving chamber 54 is also schematically illustrated in FIG. 25*a*. Assuming, that the influx of the pressurized fluid 24 into the driving chamber 54 is rather constant and assuming that the friction between the reservoir piston 23 and the inside wall of the medicament reservoir 20 is substantially constant over the displacement path of the reservoir piston 23 a force displacement diagram as illustrated in FIG. 25*b* may arise. In a region a, the pressure inside the driving chamber 54 rises from a rather low value to a threshold value p1 in an initial phase of medicament delivery. Until the pressure in the driving chamber 54 is lower than a first threshold pressure p1, the reservoir piston 23 will not move. Hence, the first pressure threshold p1 is characterized by the friction between the reservoir piston 23 and the medicament reservoir 20 as well as by the viscosity of the medicament 25 and the flow resistance downstream of the medicament reservoir, e.g. in the flexible tube 33 and in the injection needle 30.

As soon as a pressure level p1 is reached in the driving chamber 54, the reservoir piston 23 starts to move in distal direction according to the further influx of the pressurized fluid 24. In section b of the diagram the reservoir piston 23 is almost constantly moved in distal direction. In the region c, the reservoir piston 23 just temporally stops or retardates, e.g. due to locally increased friction forces, which may result from manufacturing tolerances of e.g. the medicament reservoir 20. As a consequence and as indicated by the rising slope g, the force for moving the reservoir piston 23 and hence the pressure proportional to said force rises until the reservoir piston 23 is moved further in distal direction as illustrated by the falling slope h.

Hence, due to manufacturing or geometric tolerances the displacement velocity of the reservoir piston 23 may be subject to variations. However, since the pressurized fluid 24 is compressible and since the influx of the pressurized fluid 24 into the driving chamber 54 is substantially constant, the average displacement velocity of the reservoir piston 23 during a dispensing action will be substantially constant for a large variety of medicament reservoirs 20. As further illustrated in FIG. 25*b* distally-directed displacement of the reservoir piston 23 continues over a further region d until the reservoir piston 23 hits a distal end of the medicament reservoir 20. Since the reservoir piston 23 cannot move any further in distal direction, the pressure in region e rises up to a maximum pressure pmax as indicated by the rising slope j.

Figure 26A:
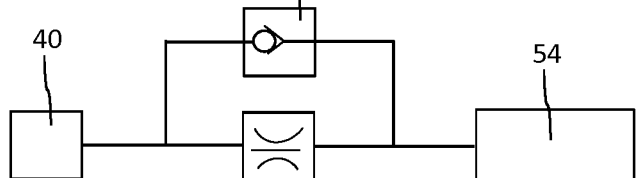
Figure 26B:
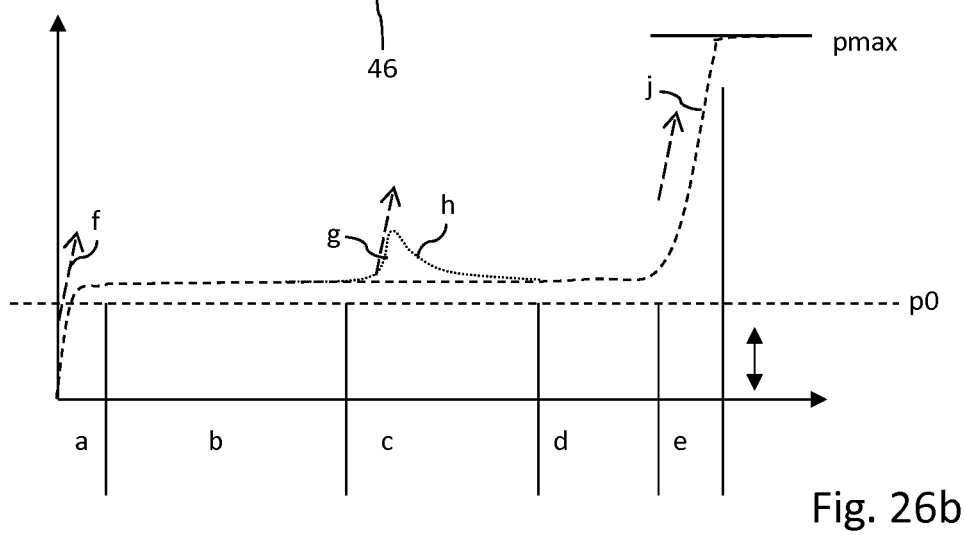

In FIGS. 26*a* and 26*b* an alternative embodiment is illustrated, wherein the flow path between the pressure container 40 and the driving chamber 54 not only comprises a throttle 46 but also a pressure-sensitive valve 36, e.g. in form of a check valve. In this embodiment, the pressure-sensitive valve 36 is substantially open below a predefined fluid pressure p0 which is only slightly smaller than the threshold pressure p1, at which the reservoir piston 23 starts to move. By means of the pressure-sensitive valve 36, the throttle 46 limiting an initial pressure build up in region a can be accelerated as indicated by the arrow f. By circumventing the throttle 46 at low pressure regions, flushing of the driving chamber 54 with the pressurized fluid 24 can be accelerated, so that reservoir piston 23 displacement and hence medicament delivery may almost immediately start after the fluid communication between the driving chamber 54 and the pressure container 40 is established.

Moreover, by providing a rather rapid initial rise of the fluid pressure inside the driving chamber 54, a respective driving momentum can be exerted to the medicament reservoir 20. Consequently, the medicament reservoir 20 can be displaced towards the stop member 51 with a well-defined velocity and impact to establish a rather rapid and loss less fluid communication between the medicament reservoir 20 and the piercing member 55.

Figure 6:
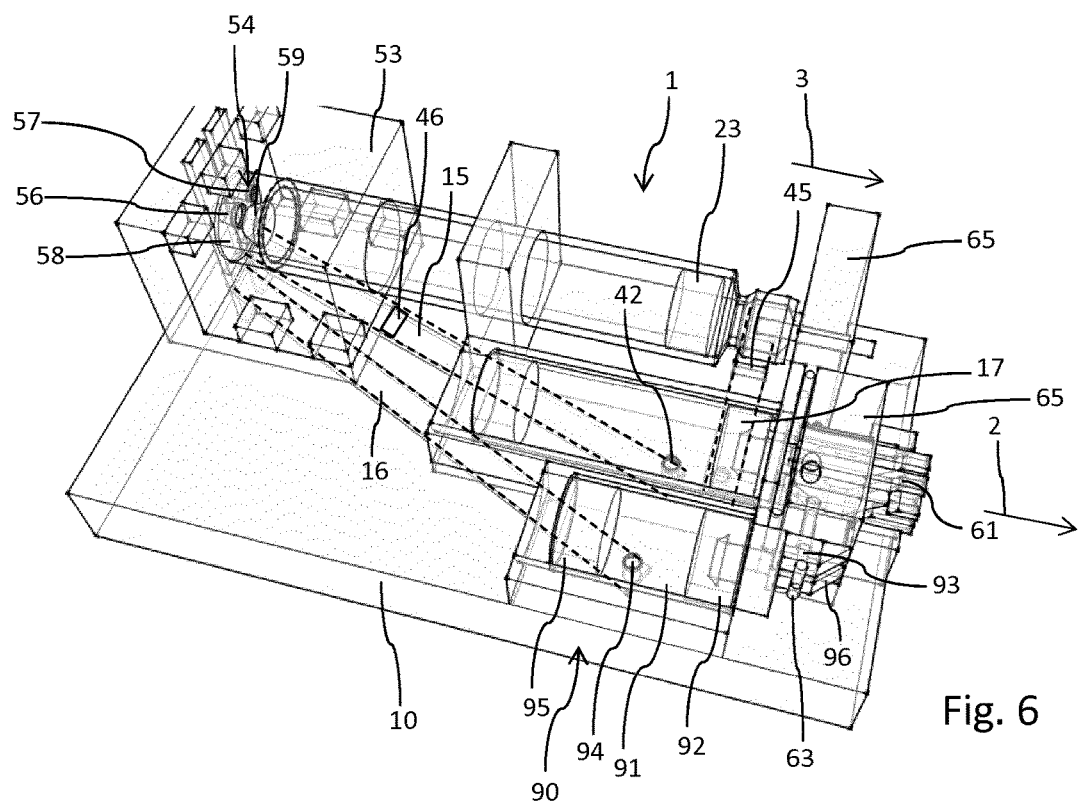
FIG. 6 is a transparent view through the injection device in a configuration after dispensing of a dose.
Figure 10:
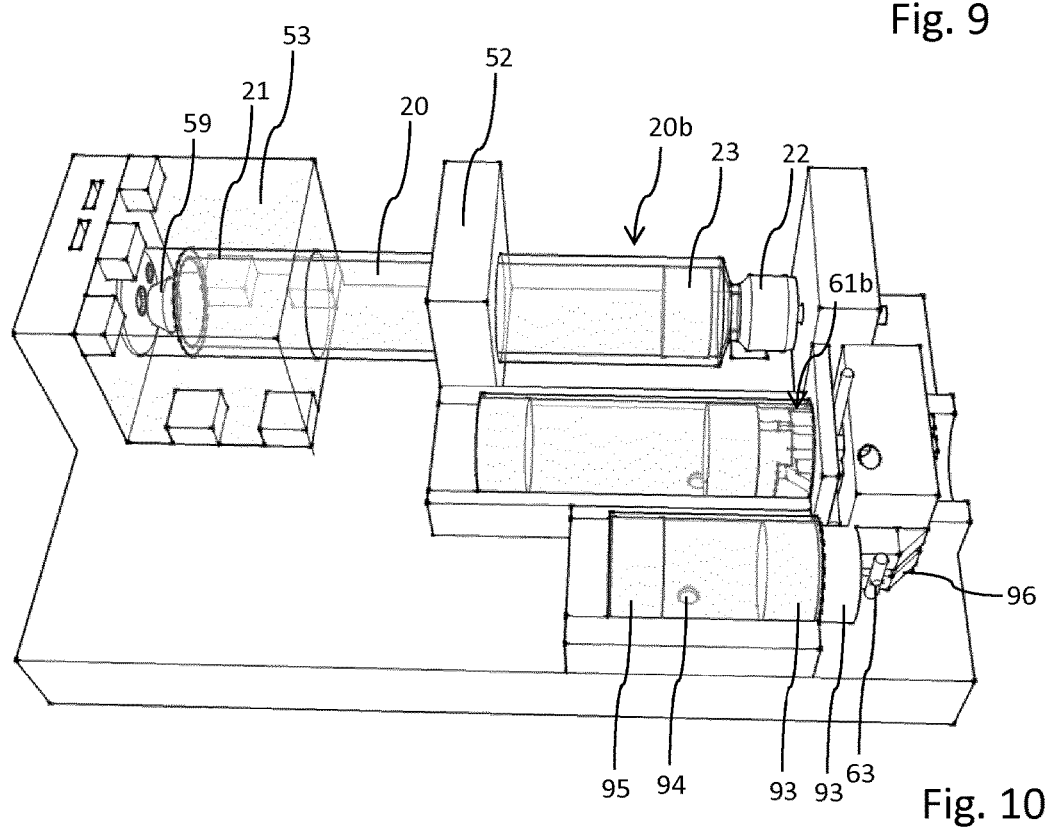
FIG. 10 shows the injection device with a deployed retraction arrangement.
Figure 11:
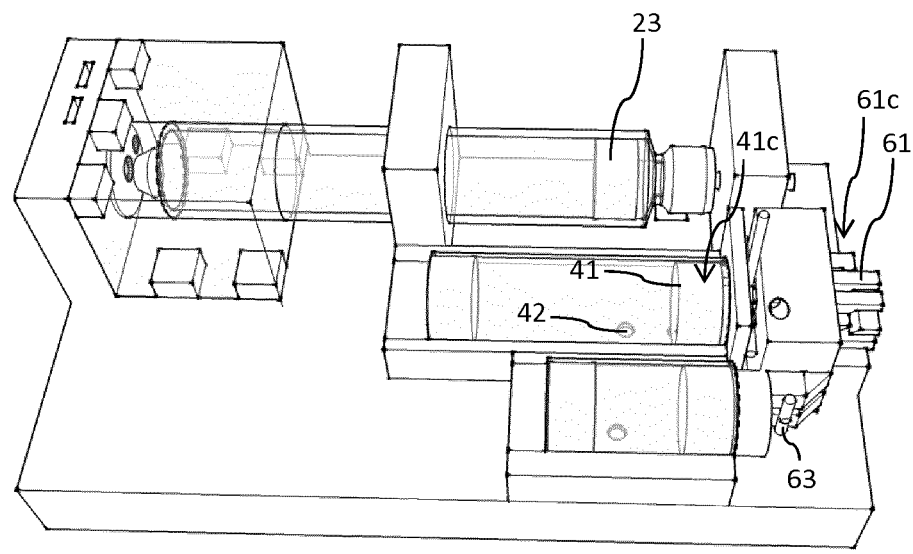
FIG. 11 shows a configuration of the injection device with the driving piston in a second extended position.

When an end of content configuration has been reached, in which the reservoir piston 23 has almost completely expelled the liquid medicament from the medicament container 20, a discharge outlet 56 in the bottom portion 58 of the driving chamber 54 is opened. In an initial configuration, as for instance illustrated in FIGS. 7-9, said discharge outlet 56 is closed and sealed by a removable plug 59. In the configuration as shown in FIG. 10, the plug 59 is axially displaced into the driving chamber 54, thereby liberating the discharge outlet 56. As further illustrated in FIG. 6, the discharge outlet 56 is in flow communication with an inlet 94 of the retraction arrangement 90, in particular of the barrel 91 as shown in FIG. 6.

The fluid communication between the discharge outlet 56 and the inlet 94 is provided by a second channel 16 which may be provided in or on the base 10. By removing the plug 59 the pressurized fluid 24 contained in the driving chamber 54 is released into the barrel 91 of the retraction arrangement, thereby displacing a release piston 92 in distal direction 3. As illustrated in FIG. 6 and as becomes apparent from a comparison of FIGS. 9 and 10, the axial displacement of the release piston 92 axially pushes the release member 93 having triangular-shaped inclined running surfaces 96 to engage with the needle stopper. Hence, the T-shaped needle stopper is displaced in radial direction and out of the horizontal slot 69 of the drive member 61 by the axial displacement of the release piston 92.

Figure 14:
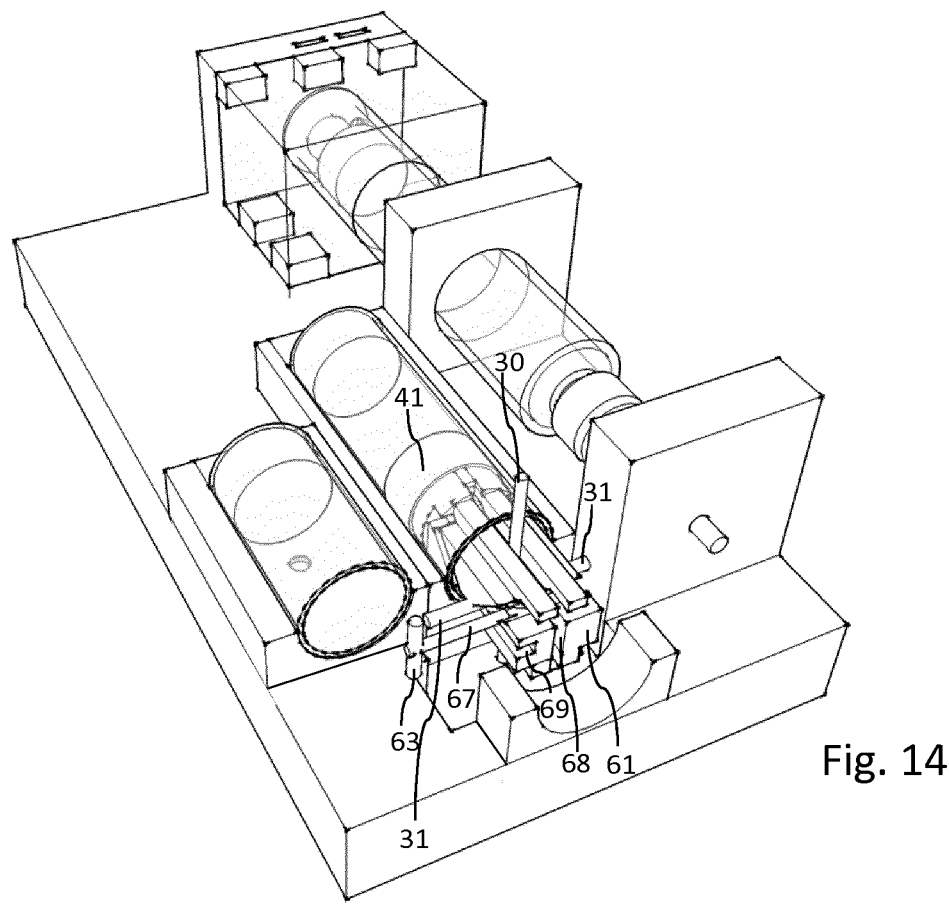
FIG. 14 shows the drive member and the injection needle in the first extended position.

Consequently and after removal of the needle stopper 63 from the drive member's 61 horizontal slot 69 the drive member 61 will be further displaced from its first extended position 61b to its second extended position 61c as illustrated in FIG. 20. In FIG. 19, a comparison of FIGS. 14 and 19 illustrates the radial or horizontal displacement of the needle stopper 63 under the action of the retraction arrangement 90. Consequently and during the further pressurized fluid 24 driven axial displacement of the drive member 61 into its second extended position 61c, the needle tappet 31 is guided in the second section 62b of the sliding block guide portion 62 of the drive member 61. Since the second section 62b features a different, in particular an opposite slope compared to the first section 62a, the needle tappet 31 and hence the injection needle 30 experiences an upward-directed displacement. Hence, the injection needle 30 is displaced from its extended position 30b into its retracted position 30a as indicated in FIG. 20.

At the same time the driving piston 41 is displaced into its second extended position 41c as indicated in FIG. 20. The driving piston 41 then reaches a distal end position. As becomes further apparent from FIGS. 6 and 20, a distal end of the drive member 61 even protrudes from the base 10 and hence from a not illustrated housing of the injection device 1 when the drive member 61 is in its second extended position 61c. In this way, a visual and haptic or tactile feedback can be provided to the user indicating the injection process has terminated.

Figure 12:
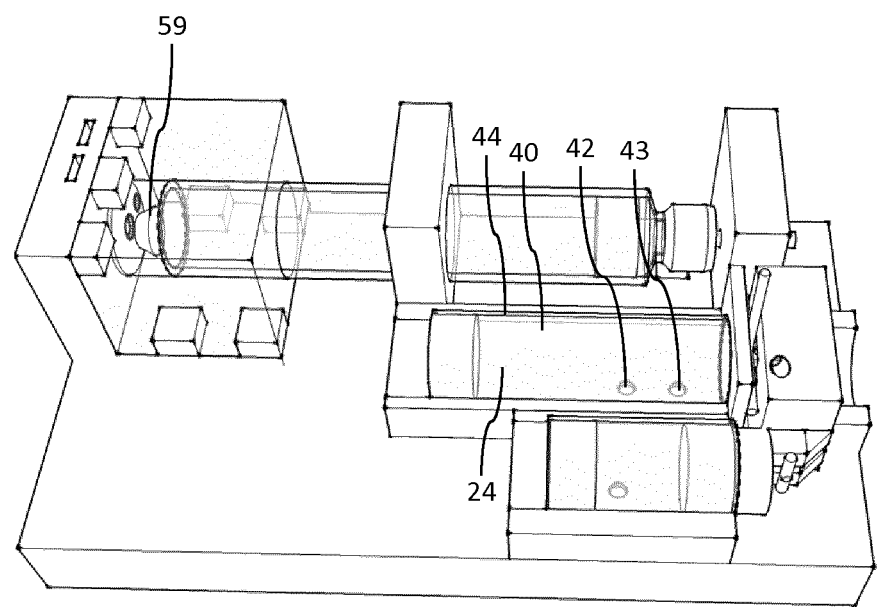
FIG. 12 shows the injection device according to FIG. 11 without the driving piston.
Figure 13:
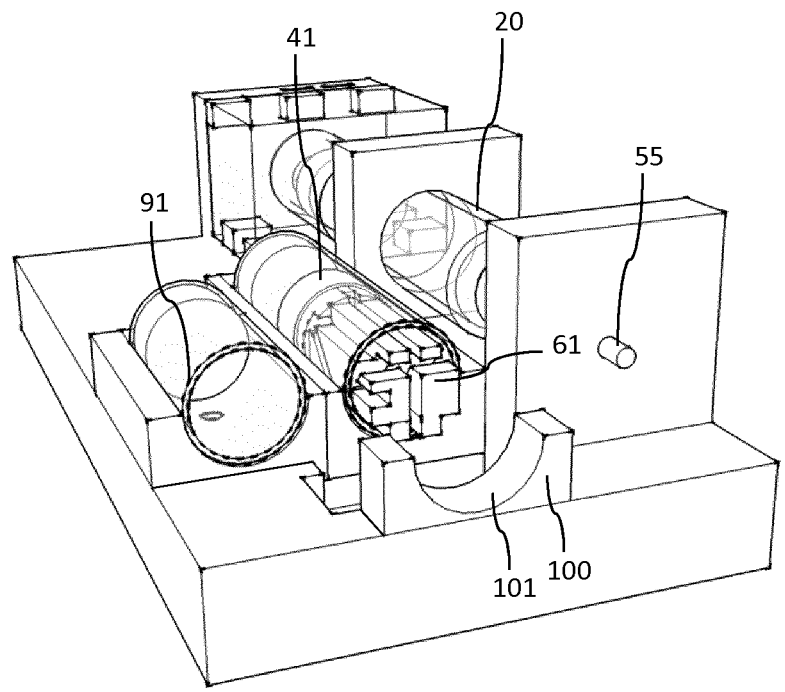
FIG. 13 shows the injection device as seen from the front with the drive member extending from the pressure container.

In addition or alternative to this visual or tactile feedback feature the pressure container 40, in particular its barrel 44 comprises a second outlet 43 as for instance shown in FIG. 12, wherein the driving piston 41 and the drive member 61 are faded out. The second outlet 43 is in fluid communication with a signal generator 45 via a third channel 17 as indicated by the dashed lines in FIG. 6. Via the third channel 17 and the signal generator 45, typically designed as whistle or the like acoustic signal generating means, the excess pressurized fluid 24 can be relieved to the environment. The outlet opening of the signal generator 45 is further shown in FIG. 5. The signal generator 45 as well as the third channel 17 may be integrated into the base 10. Typically, the base 10 is manufactured as an injection molded plastic component. In this way, at least one or several of the first, the second or the third channel 15, 16, 17 as well as the acoustic signal generator 45 may be easily integrated with a manufacturer, almost cost neutral.

The second outlet 43 is liberated as soon as the driving piston 41 reaches its second extended position 41c at the end of a dispensing procedure. In this way not only an acoustic signal indicating termination of the injection process is provided but the injection device also becomes substantially pressureless, which may be of particular benefit for discarding or recycling the injection device 1.

Typically, the injection device 1 is designed as a disposable device, which is to be entirely discarded after the injection has been executed.

For dislodging the plug 59 from the discharge outlet 56 of the driving chamber 54 it is conceivable, that the reservoir piston 23 is mechanically connected with said plug 59. For instance, the reservoir piston 23 may be connected with the plug 59 via a rope or a similar force transferring means. Upon approaching a distal end position the reservoir piston 23 will start to tighten the rope and to withdraw the plug 59 from the discharge outlet 56. In the sequence of FIGS. 21a-21d, an alternative embodiment is illustrated, wherein the medicament reservoir 20 in form of a cartridge comprises two pistons, a distal reservoir piston 23 and an additional pressure receiving piston 26. The pressure receiving piston 26 is mechanically engaged with the plug 59 via a flexible rope 27.

Figure 21A:
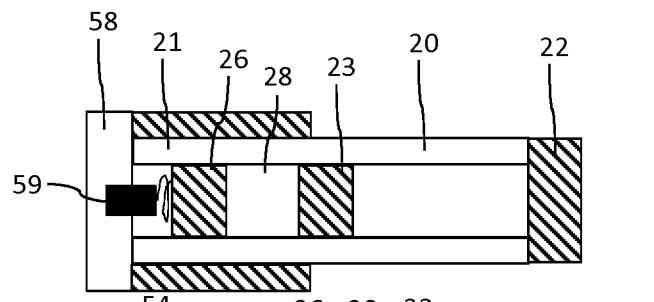
FIG. 21a shows an alternative embodiment of a medicament reservoir featuring two pistons in an initial configuration.
Figure 21B:
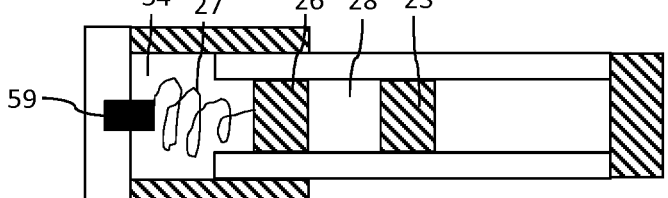
FIG. 21b shows the medicament reservoir in a dispensing position.
Figure 21C:
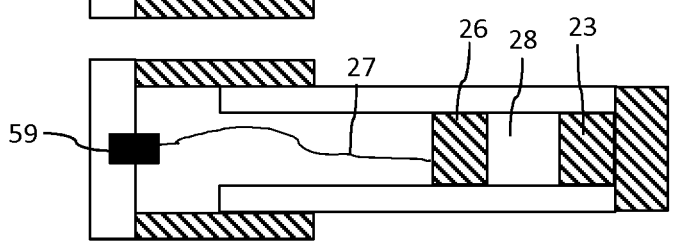
FIG. 21c shows the medicament reservoir after dispensing of the liquid medicament and FIG. 21d shows the medicament reservoir after removal of a plug, FIG. 22 schematically illustrates a pressure container with a pressure indicator in a first configuration, FIG. 23 schematically illustrates the pressure container with a pressure indicator in a second configuration, FIG. 24a schematically depicts an alternative coupling between the medicament reservoir and the driving piston at the end of a dose dispensing procedure.

In an initial configuration as illustrated in FIG. 21a, the medicament reservoir 20 is in its initial position 20a. In FIG. 21b, the pressure inside the driving chamber 54 has increased. Consequently, the medicament reservoir 20 is displaced in distal or in dispensing direction 3 until it hits and engages with the stop member 51. FIG. 21c reflects a configuration during medicament delivery. The intermediate space 28 between the two pistons 23, 26 is typically filled with a compressible substance, such like a gas. As long as the reservoir piston 23 is displaceable relative to the medicament reservoir 20, the pressure acting on the pressure receiving piston 26 is transferred via the compressible substance in the intermediate space 28 to the reservoir piston 23.

Figure 21D:
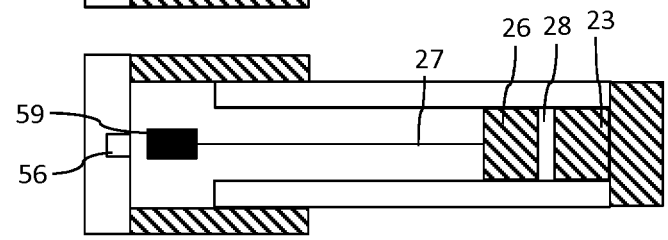

However, when an end of content configuration as depicted in FIG. 21c is reached, the reservoir piston 23 cannot move any further in distal or dispensing direction 3. In this configuration, the rope 27 is not yet strained. It is only upon a subsequent compression of the compressible substance in the intermediate space 28, that the pressure receiving piston 26 is displaced relative to the reservoir piston 23. As a consequence and as illustrated by FIG. 21d, the rope 27 will then be tense and will remove the plug 59 from the discharge outlet 56.

Alternative to the illustrated embodiment it is also conceivable to implement another check valve in the flow path between the pressure container 40 and the driving chamber 54. This check valve may operate in a sense, that it is adapted to open a discharge outlet when the pressure in the flow path rises above a maximum threshold. Opening of such a check valve would then redirect the pressurized fluid 24 of the pressure container 40 directly into the barrel 91 of the retraction arrangement 90.

Figure 24A:
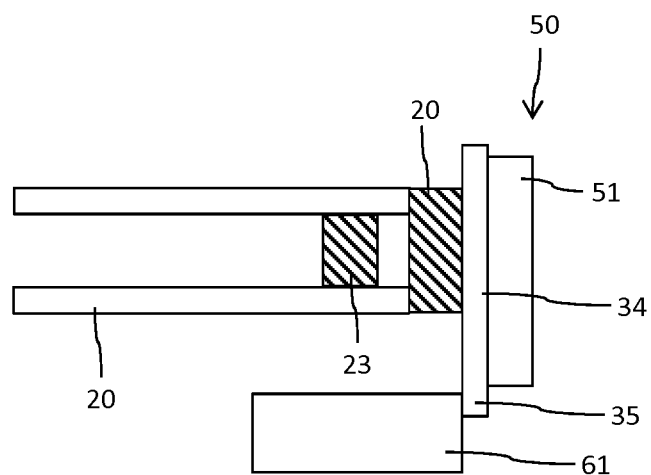
FIG. 24b shows the arrangement according to FIG. 24a after releasing the drive member, FIG. 25a schematically shows the fluid communication between the pressure container and a driving chamber of a driving unit making use of a throttle, FIG. 25b schematically shows a diagram illustrating the force or pressure applied to the reservoir piston over a piston displacement path.
Figure 24B:
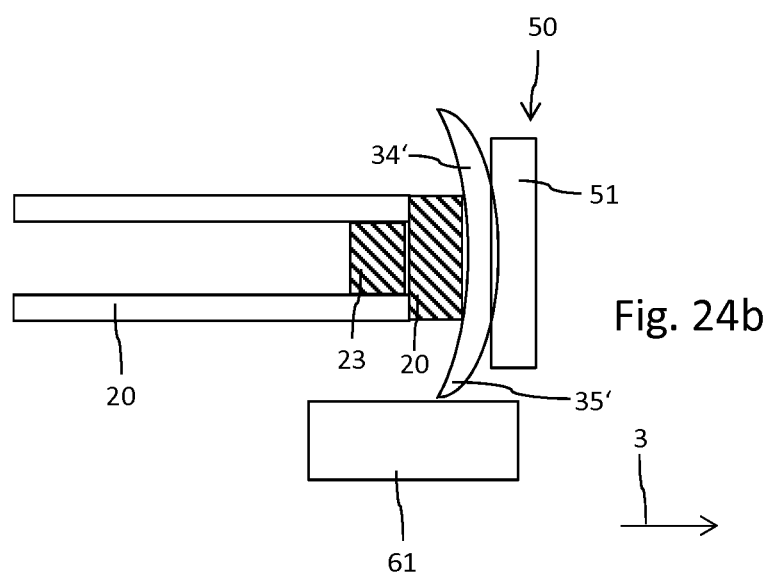

In FIGS. 24a and 24b another embodiment or configuration to establish a retraction arrangement 90 is schematically illustrated. There, the stop member 51 of the reservoir displacing arrangement 50 comprises a bending member 34 located between the distal outlet 22 of the medicament reservoir 20 and a proximal side of the stop member 51. In an initial configuration and during medicament delivery the bending member 34 features a rather planar shape and further has an end portion 35 axially engaging with the drive member 61 in a way similar as described above in connection with the needle stopper 63.

Here, the end portion 35 of the bending member 34 acts as an axial stop for the drive member 61 for keeping the drive member 61 in the first extended position 61b. As the pressure acting on the medicament reservoir 20 constantly rises at the end of the dispensing or drug delivery procedure, the bending member 34 starts to deform under the action of the rising pressure. As indicated in FIG. 24b, the bending member 34' approaches a bended geometry, whereby the end portion 35 of the bending member 34 is displaced in such a way, that the axial abutment between the bending member 34 and the drive member 61 is abrogated. Due to the mechanical deformation of the bending member 34, the drive member 61 becomes liberated and may be further displaced towards its second extended position 61c as indicated in FIG. 24b.

Figure 22:
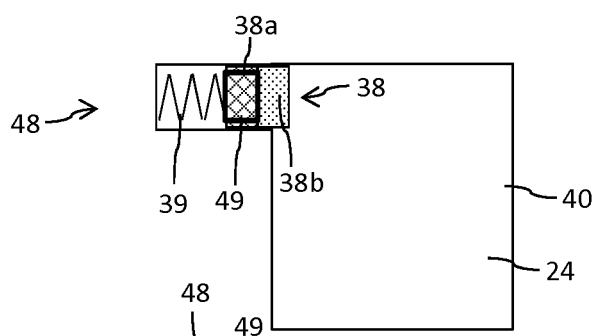
Figure 23:
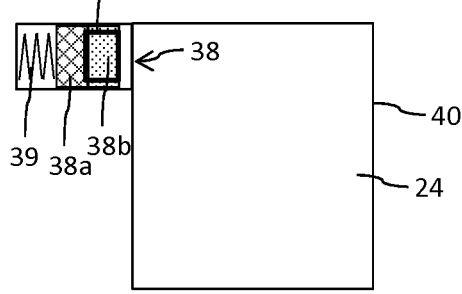

As further illustrated in FIGS. 22 and 23 the pressure container 40 can comprise or may be coupled with a pressure display 48 comprising a window 49 in which a pressure indicator 38 is displaceable against the action of a spring element 39. The pressure indicator 38 comprises at least two different pressure indicating sections 38a, 38b visually indicating if the fluid pressure inside the pressure container 40 is sufficient for conducting a dispensing procedure. The pressure indicating sections 38a, 38b are arranged next to each other in direction of a displacing direction of the spring element 39. The pressure indicator 38 is in fluid communication with the pressurized fluid 24 contained in the pressure container 40.

If the pressure of the pressurized fluid 24 is rather low, the spring element 39 will expand to a certain degree as illustrated in FIG. 22. Consequently, the pressure indicating section 38a indicating a rather low pressure will visibly appear in the window 49 of the pressure display 48. If the pressure is sufficiently high, the spring element 39 will be compressed as indicated in FIG. 23. Consequently, a different pressure indicating section 38b will appear in the window 49, thereby indicating, that the pressure of the pressurized fluid 24 is high enough to conduct a dispensing or injection procedure.

With the present injection device 1 it is of particular benefit that it comprises a minimum of mechanically displaceable components and that conventional standard cartridges may be used as medicament reservoir 20. Despite the injection device is valveless it provides a well-defined and automated sequence of injection needle displacement, medicament reservoir displacement, medicament delivery, injection needle retraction and a final visual, tactile or audible indication, that medicament delivery has terminated. In the present context, substantially valveless means a configuration wherein a user does not have to operate a valve in order to trigger subsequent steps of the injection process.

LIST OF REFERENCE NUMERALS

1 injection device
2 axial direction
3 dispensing direction
10 base
11 lower surface
12 upper surface
13 frame
14 frame
15 channel
16 channel
17 channel
20 medicament reservoir
20a initial position
20b dispensing position
21 proximal portion
22 distal outlet
23 reservoir piston
24 pressurized fluid
25 medicament
26 pressure receiving piston
27 rope
28 intermediate space
30 injection needle
30a retracted position
30b extended position
31 needle tappet
32 dispensing end
33 flexible tube
34 bending member
35 end portion
36 pressure sensitive valve
38 pressure indicator
38a indicator section
38b indicator section
39 spring element
40 pressure container
41 driving piston
41a initial position
41b extended position
41c extended position
42 outlet
43 outlet
44 barrel
45 signal generator
46 throttle
47 plug
48 pressure display
49 window
50 reservoir displacing arrangement
51 stop member
52 guiding member
53 driving unit
54 driving chamber
55 piercing member
56 discharge outlet
57 inlet
58 bottom portion
59 plug
60 needle displacing arrangement
61 drive member
61a initial position
61b extended position
61c extended position
62 sliding block guide portion
62a first section
62b second section
63 needle stopper
63a stop position
63b release position
64 slot
65 guiding structure
66 through opening
67 locking pin
68 vertical slot
69 horizontal slot
70 lock member
71 ring portion
72 shaft portion
74 fixing plate
80 safeguard member
81 gripping tab
82 shaft portion
90 retraction arrangement
91 barrel
92 release piston
93 release member
94 inlet
95 plug
96 running surface
100 support
101 support surface

The invention claimed is:

1. An injection device for dispensing of a liquid medicament, the device comprising:
a base,
a medicament reservoir displaceably arranged on the base and containing the liquid medicament,
an injection needle displaceably arranged relative to the base between a retracted position and an extended position, a pressure container containing a pressurized fluid,
a reservoir displacing mechanism coupled with the pressure container and configured to displace the medicament reservoir from an initial position, in which the medicament reservoir is not in fluid communication with the injection needle, into a dispensing position, in which the medicament reservoir is in fluid communication with the injection needle,
a needle displacing mechanism coupled with the pressure container and configured to at least displace the injection needle into the extended position, wherein the reservoir displacing mechanism and the needle displacing mechanism are separately connected with the pressure container, and
a stop member fixed to the base and configured to limit a displacement of the medicament reservoir relative to the base when the medicament reservoir reaches the dispensing position, wherein the stop member comprises a tipped piercing member to penetrate a distal outlet of the medicament reservoir when the medicament reservoir is in the dispensing position, wherein the piercing member is in fluid communication with the injection needle.

2. The injection device according to claim 1, wherein the pressure container is sealed by an axially displaceable driving piston mechanically connected to a drive member of the needle displacing mechanism, wherein the driving piston is axially displaceable from an initial position into a first extended position and into a second extended position under the effect of the pressurized fluid.

3. The injection device according to claim 2, wherein the drive member comprises at least one sliding block guide portion at least in sections extending at a predefined angle with respect to the axial direction and being engaged with a needle tappet connected to the injection needle.

4. The injection device according to claim 2, wherein the injection needle is displaceable from the retracted position into the extended position by way of an axial displacement of the driving piston from an initial position to the first extended position.

5. The injection device according to claim 2, wherein the injection needle is displaceable from the extended position into the retracted position by way of an axial displacement of the driving piston from the first extended position to the second extended position.

6. The injection device according to claim 2, wherein the pressure container comprises a first outlet in fluid communication with the reservoir displacing mechanism, wherein the first outlet is sealed by the driving piston when the driving piston is in the initial position and wherein the first outlet is at least partially in fluid communication with the pressurized gas when the driving piston is in the first extended position.

7. The injection device according to claim 2, wherein the reservoir displacing mechanism comprises:
a stop member, and
a driving unit hydraulically or pneumatically coupleable with the pressure container and comprising a driving chamber to slidably receive a proximal portion of the medicament reservoir.

8. The injection device according to claim 7, wherein the medicament reservoir comprises a rigid body proximally sealed by a reservoir piston, which is displaceable in a medicament dispensing direction by way of the pressurized fluid flowing into the driving chamber of the driving unit of the reservoir displacing mechanism.

9. The injection device according to claim 2, further comprising a locking member extending with a shaft portion through the needle displacing mechanism to block a distally directed displacement of the pressure container's driving piston.

10. The injection device according to claim 2, further comprising a retraction mechanism mechanically engaged with a needle stopper to displace the needle stopper into a release position, in which the driving piston is displaceable into the second extended position.

11. The injection device according to claim 10, wherein the retraction mechanism comprises a barrel sealed by a displaceable release piston operably engageable with the needle stopper, wherein the barrel comprises an inlet in fluid communication with a discharge outlet of the reservoir displacing mechanism.

12. The injection device according to claim 2, wherein the pressure container comprises a second outlet in fluid communication with a signal generator, wherein the second outlet is at least partially in fluid communication with the pressurized fluid when the driving piston is in the second extended position, wherein the reservoir displacing mechanism and the needle displacing mechanism are separately connected with the pressure container.

13. The injection device according to claim 1, further comprising at least one throttle arranged in a flow path between the pressure container and the medicament reservoir to control a rate of medicament dispensing.

14. An injection device for dispensing of a drug, the device comprising:
a base,
a medicament reservoir displaceably arranged on the base and containing a pharmaceutically active compound,
an injection needle displaceably arranged relative to the base between a retracted position and an extended position,
a pressure container containing a pressurized fluid,
a reservoir displacing mechanism coupled with the pressure container and configured to displace the medicament reservoir into a dispensing position, in which the medicament reservoir is in fluid communication with the injection needle, and
a needle displacing mechanism coupled with the pressure container and configured to at least displace the injection needle into the extended position, wherein the reservoir displacing mechanism and the needle displacing mechanism are separately connected with the pressure container,
wherein the pressure container is sealed by an axially displaceable driving piston mechanically connected to a drive member of the needle displacing mechanism, wherein the driving piston is axially displaceable from an initial position into a first extended position and into a second extended position under the effect of the pressurized fluid, and
wherein the pressure container comprises a first outlet in fluid communication with the reservoir displacing mechanism, wherein the first outlet is sealed by the driving piston when the driving piston is in the initial position and wherein the first outlet is at least partially in fluid communication with the pressurized gas when the driving piston is in the first extended position.

15. A method of operating an injection device, the method comprising:
removing a stop from a piston of a pressure container;
moving the piston of the pressure container with a pressurized fluid in the pressure container from a rest position to a first position in the pressure container, the first position fluidly coupling the pressurized fluid to a medicament reservoir;

displacing the medicament reservoir into abutment with a stop member being fixed to a base, the base comprising a tipped piercing member, penetrating a distal outlet of the medicament by the tipped piercing member, wherein the tipped piercing member is in fluid communication with an injection needle;

advancing a needle through a base of the injection device as the piston moves to the first position;

moving the piston of the pressure container with the pressurized fluid to a second position in the pressure container; and driving a medicament from the medicament reservoir and injecting the medicament through the needle as the piston moves to the second position, wherein the medicament reservoir is displaced into the fluid communicating engagement with the injection needle independent of advancing the needle through the base of the injection device.

16. An injection device for dispensing of a liquid medicament, the device comprising:

a base, a medicament reservoir displaceably arranged on the base and containing the liquid medicament, an injection needle displaceably arranged relative to the base between a retracted position and an extended position, a pressure container containing a pressurized fluid, a reservoir displacing mechanism coupled with the pressure container and configured to displace the medicament reservoir into a dispensing position, in which the medicament reservoir is in fluid communication with the injection needle, and a needle displacing mechanism coupled with the pressure container and configured to at least displace the injection needle into the extended position, wherein the reservoir displacing mechanism and the needle displacing mechanism are separately connected with the pressure container, and at least one throttle arranged in a flow path between the pressure container and the medicament reservoir to control a rate of medicament dispensing.

* * * * *

UNITED STATES PATENT AND TRADEMARK OFFICE
CERTIFICATE OF CORRECTION

PATENT NO. : 10,251,997 B2
APPLICATION NO. : 15/026708
DATED : April 9, 2019
INVENTOR(S) : Christian Nessel and Daniel Auernhammer It is certified that error appears in the above-identified patent and that said Letters Patent is hereby corrected as shown below:

In the Claims

Column 31, Line 7, Claim 15, after "medicament" insert -- reservoir --

Signed and Sealed this
Thirtieth Day of July, 2019

Andrei Iancu
*Director of the United States Patent and Trademark Office*